(12) United States Patent
Hau et al.

(10) Patent No.: US 11,906,509 B2
(45) Date of Patent: Feb. 20, 2024

(54) NANOPORE-MATCHED PROTEIN SHUTTLE FOR MOLECULAR CHARACTERIZATION AND METHODOLOGY FOR DATA ANALYSIS THEREOF

(71) Applicant: PRESIDENT AND FELLOWS OF HARVARD COLLEGE, Cambridge, MA (US)

(72) Inventors: Lene V. Hau, Cambridge, MA (US); Jene A. Golovchenko, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 18/122,887

(22) Filed: Mar. 17, 2023

(65) Prior Publication Data
US 2023/0349883 A1    Nov. 2, 2023

Related U.S. Application Data

(63) Continuation of application No. 16/629,644, filed as application No. PCT/US2018/042480 on Jul. 17, 2018, now Pat. No. 11,639,922.
(Continued)

(51) Int. Cl.
G01N 33/487    (2006.01)

(52) U.S. Cl.
CPC ............... *G01N 33/48721* (2013.01)

(58) Field of Classification Search
CPC ............. B82Y 15/00; G01N 33/48721; G01N 33/6872; G01N 33/487; C12Q 1/6869; C12Q 2565/631
See application file for complete search history.

(56) References Cited

U.S. PATENT DOCUMENTS

| 11,639,922 B2 * | 5/2023 | Hau | G01N 33/6872 |
| | | | 702/19 |
| 2009/0136958 A1 | 5/2009 | Gershow et al. | |

(Continued)

FOREIGN PATENT DOCUMENTS

WO    2016/196625 A1    12/2016

OTHER PUBLICATIONS

Lu et al., "Dynamics of a Form-Fitting Protein in a Nanopore: Avidin in ClyA." bioRxiv (2017): pp. 1-30.
(Continued)

*Primary Examiner* — Jermele M Hollington
*Assistant Examiner* — Suresh K Rajaputra
(74) *Attorney, Agent, or Firm* — NIXON PEABODY LLP; David S. Resnick; Wayne L. Tang

(57) ABSTRACT

Systems and methods are provided for characterizing shuttle capture events in a nanopore sensor. The method first collects time-dependent current blockage signatures for at least one bias voltage. The method then identifies each signature as corresponding to a permanent or transient event. The method then generates a protein dynamics landscape (PDL) for the transient event signatures. The PDL comprises a set of histograms of nanopore current data and characterizes current through the nanopore during shuttle capture events. The method can then comprise identifying an entrance level blockage value based on the permanent event signatures. Permanent event captures can be determined by time duration which is larger than a certain threshold time value. Applying a voltage between the fluidic chambers above a threshold voltage level can be used to control that the vast majority of events are permanent.

19 Claims, 27 Drawing Sheets

Related U.S. Application Data

(60) Provisional application No. 62/533,215, filed on Jul. 17, 2017.

(56) References Cited

U.S. PATENT DOCUMENTS

| | | | |
|---|---|---|---|
| 2010/0148126 A1* | 6/2010 | Guan | G01N 33/48721 548/335.1 |
| 2011/0226623 A1* | 9/2011 | Timp | G01N 27/4146 204/543 |
| 2014/0246317 A1 | 9/2014 | Mayer et al. | |
| 2014/0364324 A1 | 12/2014 | Turner et al. | |
| 2015/0080242 A1 | 3/2015 | Chen et al. | |
| 2016/0053300 A1 | 2/2016 | Maglia et al. | |
| 2017/0022546 A1 | 1/2017 | Bashir et al. | |
| 2021/0148884 A1* | 5/2021 | Hau | G01N 27/44791 |

OTHER PUBLICATIONS

Franceschini et al., "A nanopore machine promotes the vectorial transport of DNA across membranes." Nature communications (4): 2415 pp. 1-8 (2013).

Franceschini et al., "DNA translocation through nanopores at physiological ionic strengths requires precise nanoscale engineering." ACS nano 10(9): 8394-8402 (2016).

Ghadiari et al., "Single DNA Rotaxanes of a Transmembrane Pore Protein", Angewandte Chemie International Edition, 43(23): 3063-3067 (2004).

An et al. "Crown ether-electrolyte interactions permit nanopore detection of individual DNA abasic sites in single molecules." Proceedings of the National Academy of Sciences 109(29): 11504-11509 (2012).

Butler et al., "Determination of RNA orientation during translocation through a biological nanopore." Biophysical Journal 90(1): 190-199 (2006).

Fahie et al., "Tuning the selectivity and sensitivity of an OmpG nanopore sensor by adjusting ligand tether length." ACS sensors 1.5 (2016): 614-622.

Jain et al. "Comparison of avidin, neutravidin, and streptavidin as nanocarriers for efficient siRNA delivery." Molecular pharmaceutics 14(5): 1517-1527 (2016).

Jetha et al., "Long dwell-time passage of DNA through nanometer-scale pores: kinetics and sequence dependence of motion." Biophysical journal 100.12 (2011): 2974-2980.

Kasianowicz et al., "Simultaneous multianalyte detection with a nanometer-scale pore." Analytical Chemistry 73.10 (2001): 2268-2272.

Maglia et al., "Engineering a biomimetic biological nanopore to selectively capture folded target proteins." Biophysical Journal 104.2 Supp 1 (2013): 518a, Abstract 2657.

Sanchez-Quesada et al., "Cyclic peptides as molecular adapters for a pore-forming protein." Journal of the American Chemical Society 122.48 (2000): 11757-11766.

Soskine et al., "An engineered ClyA nanopore detects folded target proteins by selective external association and pore entry." Nano letters 12.9 (2012): 4895-4900.

Soskine et al., "Single-molecule analyte recognition with ClyA nanopores equipped with internal protein adaptors." Journal of the American Chemical Society 137.17 (2015): 5793-5797.

Wloka et al., "Label-free and real-time detection of protein ubiquitination with a biological nanopore." ACS nano 11.5 (2017): 4387-4394.

\* cited by examiner

NANOPORE-MATCHED PROTEIN SHUTTLE FOR MOLECULAR CHARACTERIZATION AND METHODOLOGY FOR DATA ANALYSIS THEREOF

CROSS-REFERENCE TO RELATED APPLICATIONS

This application is a continuation under 35 U.S.C. § 120 of co-pending U.S. application Ser. No. 16/629,644, filed Jan. 9, 2020, which is a 371 National Phase Entry of International Patent Application No. PCT/US2018/042480, filed Jul. 17, 2018, which claims priority to and the benefit of U.S. Provisional Patent Application No. 62/533,215, filed Jul. 17, 2017 and entitled "Nanopore-Matched Protein Shuttle for Molecular Characterization and Methodology for Data Analysis Thereof," the contents of each of which are hereby incorporated by reference in their entirety as if fully set forth herein.

FIELD

The present invention relates to systems and methods for characterizing a nanopore sensor and for analyzing and visualizing single molecule measurements obtained with the sensor.

BACKGROUND

Molecules can be trapped and electrically monitored via a nanopore. In particular, protein shuttles, typically including a protein molecule and other molecules of interest attached to the protein molecule, can be induced to bind with a voltage-biased nanopore. The protein shuttle can enable monitoring of the molecules of interest. However, nanopore-based study of molecules is challenging due to the complex geometrical and electrical charge structures of protein molecules in protein shuttles. The complex structures make it difficult to stably trap a protein molecule in a nanopore. Additionally, artificially reproduced nanopores and nanopore-holding structures typically encounter difficulties with the sizing of the nanopore, a stability of the bond between the nanopore and the protein molecule, noise characteristics, and other chemical, mechanical, electrical, and thermal constraints.

To effectively monitor the protein molecules or other molecules of interest at a nanopore, systems and methods are needed to induce and maintain trapping of the molecules at the nanopore. Effective analysis and visualization techniques are also needed to analyze large amounts of global molecule events to reveal the dynamics of a protein shuttle system and/or molecules of interest.

SUMMARY

The various examples of the present disclosure are directed towards a method for characterizing shuttle capture in a nanopore sensor. The method can comprise collecting a plurality of time-dependent current blockage signatures for a plurality of different bias voltages. The method can then comprise classifying the plurality of time-dependent current blockage signatures into permanent event signatures and transient event signatures. For each of the plurality of bias voltages, a protein dynamics landscape (PDL) can be generated for the transient event signatures. The PDL comprises a collection of blockage spectra. Each of the collection of blockage spectra can comprise a histogram of blockage values for transient events of a selected maximum duration. The method can further comprise, generating for each of the plurality of bias voltages, a protein dynamics landscape (PDL) for the permanent event signatures. The PDL comprises a collection of blockage spectra. Each of the collection of blockage spectra can comprise a histogram of blockage values for permanent events where these blockage values are obtained for each permanent event from the start of the event and up to a maximum time after event start. The method can then comprise identifying a permanent level blockage value based on permanent event signatures. The permanent blockage level is a blockage level that, once reached, rarely ever changes unless the shuttle is ejected, for example, by reversing the polarity of the applied voltage. The method can further comprise identifying an entrance level blockage value based on permanent event signatures and the PDL plots for the permanent events. The method can then comprise selecting one of the plurality of bias voltages corresponding to a PDL for the transient event signatures. The collection of blockage spectra can reveal peaks at blockage values that are substantially equal to the permanent level blockage value and/or to the entrance level blockage value.

In some examples, the time-dependent current blockage signature comprises a measurement of nanopore current as a function of time during a shuttle capture event.

In some examples, the classifying can comprise identifying as transient event signatures any one of the plurality of time-dependent current blockage signatures which shows a return to an initial current level. The classifying can comprise identifying as the permanent event signatures any one of the plurality of time-dependent current blockage signatures failing to show a return to an initial current level.

In some examples, the method can further comprise calculating a ratio of a number of permanent shuttle capture events to a number of transient shuttle capture events for each of the plurality of bias voltages. Based on the calculated ratios, the method can then comprise determining a threshold bias voltage to achieve a preferred ratio.

In some examples, the blockage spectra can comprise an average of nanopore current blockage data sampled over a fixed time interval to yield histogram data points. The fixed time interval can be at least as large as an interval for sampling the nanopore current blockage data. The nanopore current blockage data can comprise a ratio of a change in the current from an input current to the input current.

In some examples, the identifying step can comprise generating an additional PDL for the permanent event signatures for at least one of the plurality of bias voltages. The identifying step can further comprise selecting an entrance level blockage value to correspond to a blockage level lower than the permanent blockage level.

In some examples, the method can further comprise fitting each spectrum of the collection of blockage spectra within a PDL with a sum of Gaussian distributions. The entrance level blockage value can be determined from a peak in the collection of blockage spectra within the PDL for permanent events.

In some examples of the first embodiment, the selected maximum duration of the events included in generating particular blockage spectra of a PDL for transient events can be 2 milliseconds, 5 milliseconds 10 milliseconds, 30 milliseconds, 100 milliseconds, 500 milliseconds, and 1000 milliseconds.

In a second embodiment of the present disclosure, a method can be provided for characterizing shuttle capture in a nanopore sensor. The method can comprise first collecting a plurality of time-dependent current blockage signatures for a selected bias voltage. The method can then provide for calculating, based on the plurality of time-dependent current blockage signatures, a duration of a shuttle capture event and a blockage percentage or an average blockage percentage for the shuttle capture event. The method can then provide for determining a blockage level based on a distribution characteristic of the plurality of time-dependent current blockage signatures.

In some examples, the determining step can comprise determining whether the duration of the shuttle capture event falls in a range between a pre-defined minimum duration and a pre-defined maximum duration.

The pre-defined minimum duration can be 0 milliseconds and the pre-defined maximum duration can be 2 milliseconds. This can provide a blockage peak in the blockage spectrum for shuttle capture events in this category at 40% current blockage.

The pre-defined minimum duration can be 0 milliseconds and the pre-defined maximum duration can be 5 milliseconds. This can provide additional blockage peaks in the blockage spectrum at 45% and 52% blockages.

The pre-defined minimum duration can be 0 milliseconds and the pre-defined maximum duration can be 10 milliseconds. This can provide blockage peaks at 40%, 45%, and 52% blockages.

The pre-defined minimum duration can be 0 milliseconds and the pre-defined maximum duration can be 30 milliseconds. This can provide an additional blockage peak at a blockage level of 57%.

The pre-defined minimum duration can be 0 milliseconds and the pre-defined maximum duration can be 100 milliseconds. This can provide blockage levels at 40%, 45%, 52%, and 57%.

The pre-defined minimum duration can be 0 milliseconds and the pre-defined maximum duration can be 500 milliseconds. This can provide blockage levels at 40%, 45%, 52%, and 57%.

The pre-defined minimum duration can be 0 milliseconds and the pre-defined maximum duration can be 1000 milliseconds. This can provide an additional blockage level at 80%.

In some examples, the method can identify an expected protein molecule orientation based on at least one of a comparison of the PDLs for transient and permanent events and a presence or absence of blockage peaks for individual spectra within the PDLs for transient and permanent events.

In some examples, the determining step can comprise identifying a particular blockage event as permanent if the duration of the particular blockage event is larger than a threshold time. The threshold time can be any time value larger than 500 milliseconds in one implementation.

The term "protein shuttle" is used herein interchangeably with the term "molecular shuttle."

In the present disclosure, the term "shuttle capture" refers to when at least one molecule is trapped at a nanopore.

BRIEF DESCRIPTION OF THE DRAWINGS

The accompanying drawings exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

DETAILED DESCRIPTION

Figure 1A:
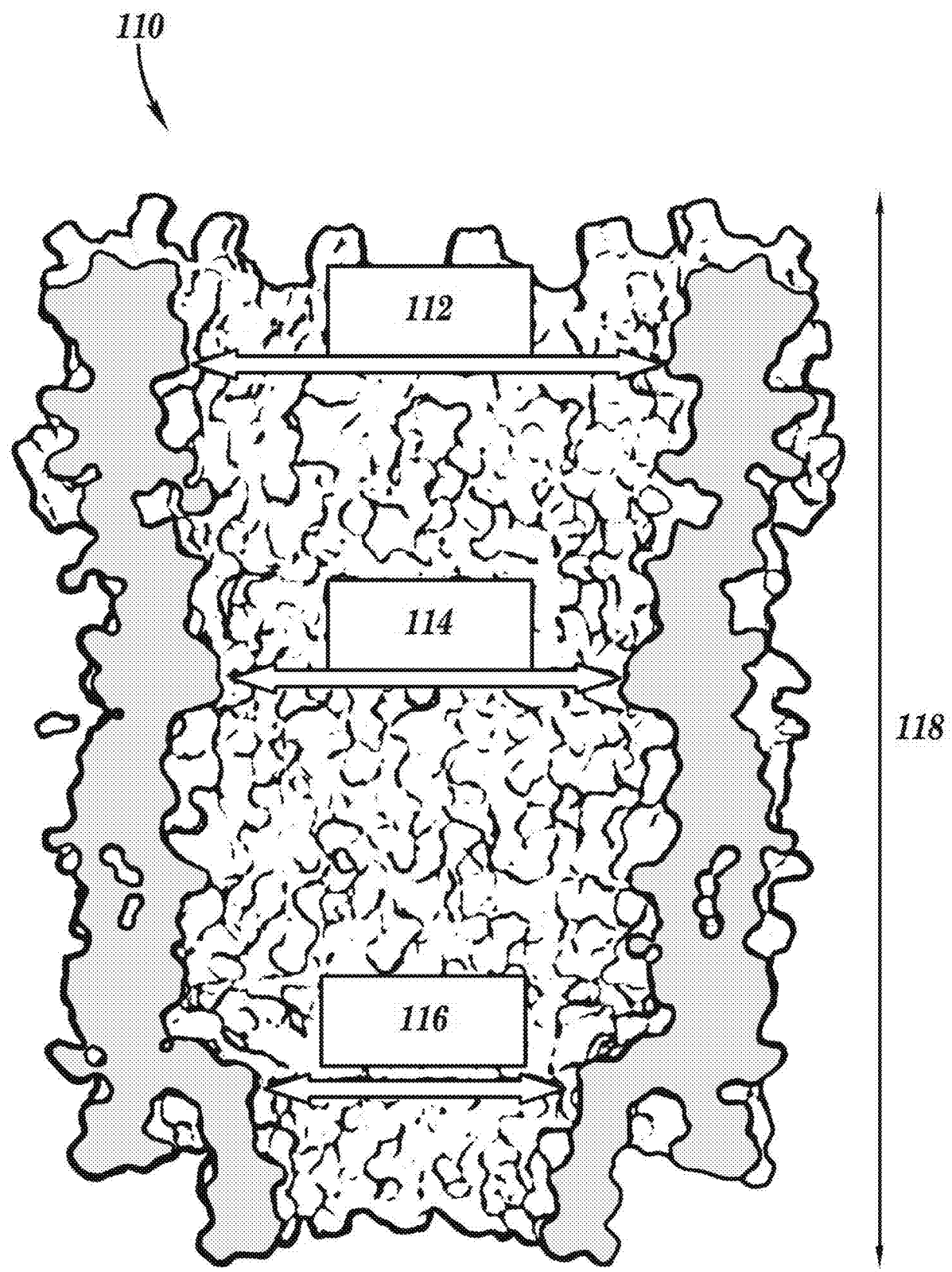
FIG. 1A shows an exemplary ClyA nanopore.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The present disclosure is directed to a method for characterizing shuttle capture events in a nanopore sensor. The method first collects a plurality of time-dependent current blockage signatures for a plurality of different bias voltages. These time-dependent current blockage signatures can show whether a particular shuttle capture event is a permanent or transient event. The method can then generate a protein dynamics landscape (PDL) for the transient event signatures. The PDL comprises a histogram of nanopore current data and characterizes current through the nanopore during shuttle capture events. The method can then comprise identifying an entrance level blockage value based on the permanent event signatures. This entrance level blockage value can indicate the minimum necessary blockage that a protein shuttle needs to have when entering a nanopore in order for the nanopore to permanently capture the protein shuttle. This information can then be used to select a particular voltage to cause that particular entrance level blockage value.

Therefore, the present disclosure provides a detailed analysis method to characterize a nanopore sensor, including levels of blockage of a protein molecule and how the sensor interacts with different voltages. The analysis can guide interaction with the nanopore sensor to select certain voltages in order to obtain corresponding ratios of permanent to transient event captures and even to obtain certain configurations of a protein shuttle's entry into the nanopore.

The present disclosure provides systems and methods for observing and measuring individual, electrically-charged biological molecules as they translocate through a voltage-biased nanopore in a lipid membrane by monitoring the ionic conductance of the nanopore during the molecular motion through the nanopore. These measurements provide new insights into the biophysics of these molecules and their interactions with nanopores. An embodiment of the present disclosure can be used in practical, portable instruments for sequencing DNA, when a DNA strand is attached to the protein shuttle as the target molecule. Therefore, the present disclosure provides for probing the molecule of interest linked to the shuttle, and probing the dynamics of the molecule of interest linked to the shuttle.

FIG. 1A shows the protein structure an exemplary nanopore 110 with an inlet diameter 112, an inner lumen diameter 114, an outlet diameter 116, and a length 118.

An exemplary nanopore 110 can comprise ClyA dodecamer. ClyA is a pore-forming cytolytic toxin expressed in several pathogenic strains of *Escherichia coli* and *Salmonella enterica*. ClyA has 12 soluble monomers. Upon reaching a target-cell membrane, the soluble monomers undergo significant conformational changes, involving half of the monomers' amino acid residues, and subsequently assemble into membrane-bound oligomers. The resulting membrane-spanning ClyA pores form nanometer-sized circular holes in the membrane. FIG. 1A shows an exemplary cross-sectional view of ClyA after the ClyA has configured as a pore. The cross-sectional view reveals the twelve-fold rotational symmetry axis of the ClyA nanopore after the ClyA nanopore formed a circular hole. Once ClyA configures as a pore in a lipid membrane of a cell, the lipid membrane's function as a cell barrier is lost, and this ultimately leads to cell death. The nanometer-sized circular hole is referred to herein as a nanopore.

A ClyA nanopore can have different diameters for different interior portions of the nanopore. For example, as shown in FIG. 1A, the inlet diameter 112 of nanopore 110 can be a different width than the inner lumen diameter 114 and both can be different than the outlet diameter 116. In some examples, the inner lumen diameter 114 can be smaller than the inlet diameter. Further, the outlet diameter 116 can be smaller than both the inlet diameter 112 and the inner lumen diameter 114. In general, the inner lumen diameter 114 is not constant along the length of the lumen. For example, the ClyA inner lumen diameter can range from 4.1 nm outlet diameter 116 to 6.5 nanometers (nm) inlet diameter 112. Additionally, an exemplary inner lumen diameter 114 can be 5.4 nm. The ClyA nanopore 112 can have an open-pore conductance when configured in a lipid membrane or other support structures.

Although the ClyA dodecamer is shown and referred to in the present application as an example nanopore, many different oligomers of ClyA exist. The ClyA 8'mer, ClyA 13'mer, ClyA 14'mer, the tetramer ClyA, and other oligomers can also be employed. Each oligomeric form can have different diameters 112, 114, and 116 and can have a unique open-pore conductance due to its geometric size and the charges of the monomers in the particular nanopore. The features of a nanopore in FIG. 1A and referred to subsequently in the present disclosure are not therefore limited to a particular ClyA oligomer or to ClyA specifically. Any nanopore can be used so long as the nanopore can trap a molecule of interest, including a protein shuttle.

Figures 1B, 1C, 1D:
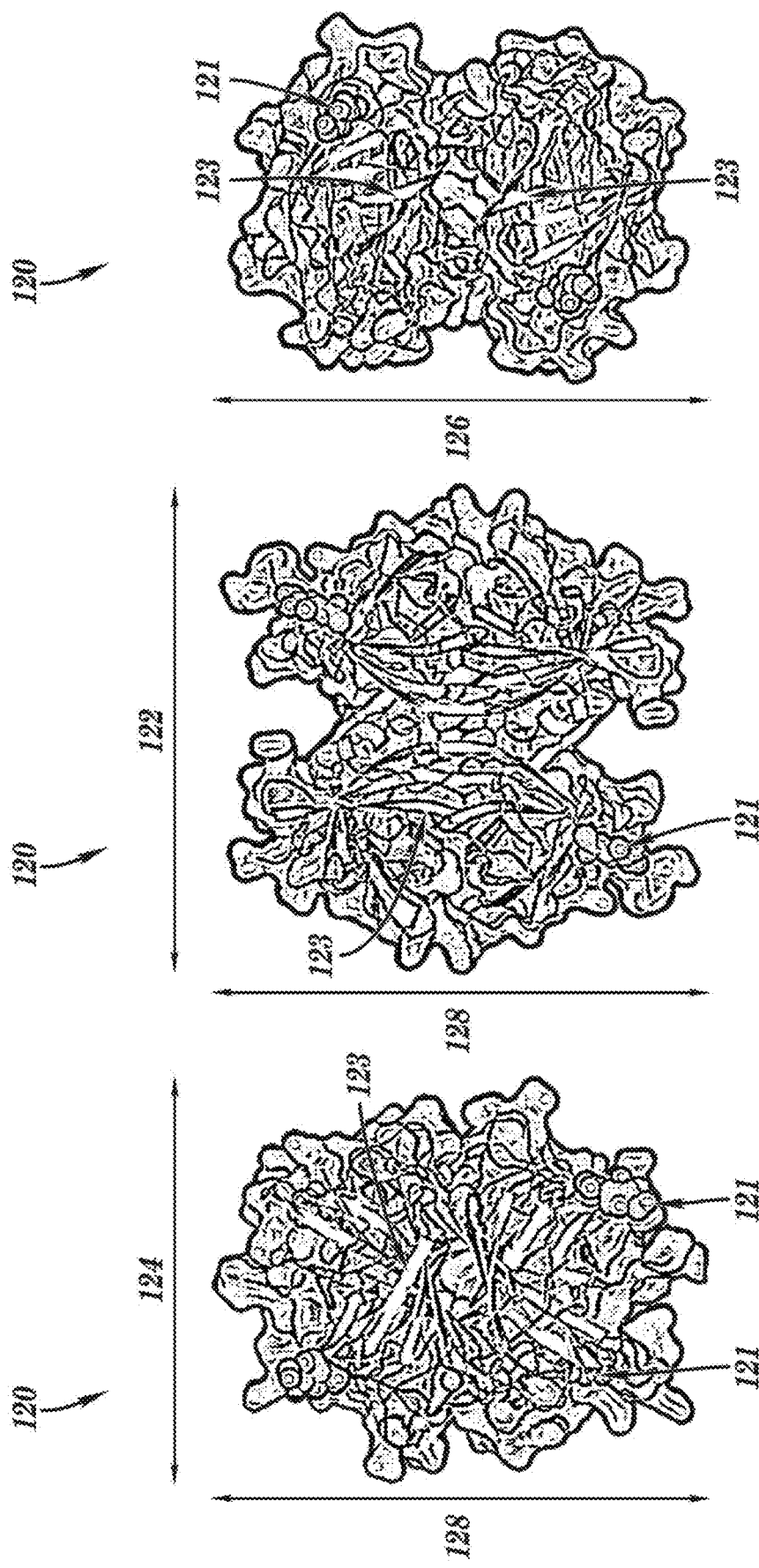
FIG. 1B shows a first perspective view of the protein Avidin.
FIG. 1C shows a second perspective view of the protein Avidin.
FIG. 1D shows a third perspective view of the protein Avidin.

FIGS. 1B-1D show various perspective views of a protein 120 with a first dimension 122, a second dimension 124, a third dimension 126, and a fourth dimension 128. For example, FIG. 1B shows a first orientation, FIG. 1C shows a second orientation, and FIG. 1D shows a third orientation. Protein 120 can comprise Avidin, which is commercially available, e.g., Pierce Avidin, ThermoFisher Scientific, and can be purified from hen egg white.

FIGS. 1B-1D show how Avidin is usually a glyco-protein tetramer which further comprises four beta barrels 123, which are ribbon-like structures. Selected orientations of Avidin can have an open beta barrel 123 open at each end of Avidin. Avidin can also be monomeric, dimeric, and trimeric, and all of these forms can be employed as described herein. Avidin can comprise one asparagine glycosylation binding site 121 per monomer. Avidin has a polysaccharide attached to each of the four binding sites 121. In addition to the core GlcNAc, the polysaccharides have 4-5 mannose and 2 GlcNAc. Avidin has an electrical charge of roughly 7 positive charges at the pH of 7.5. In other implementations, deglycosylated avidin can be used.

The positive charge of Avidin allows Avidin to bind with a negatively charged molecule. Additionally, the dimensions 122, 124, 126, and 128 of the protein molecule 120 can be paired to match interior diameters of a nanopore such that the protein molecule 120 can fit within a nanopore. For example, a first dimension 122 can be 6.8 nm, a second dimension 124 can be 5.5 nm, a third dimension 126 can be 6.7 nm, and a fourth dimension 128 can be 7.1 nm.

Although Avidin is referenced as an exemplary protein molecule for purposes of the present application, any protein molecule can be used so long as the protein molecule can attach to a nanopore and block at least some of the current through the nanopore.

Figure 1E:
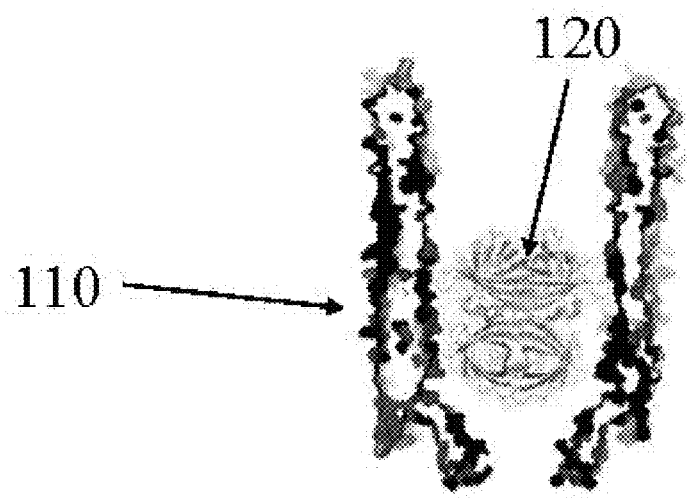
FIG. 1E shows a cutout view of an exemplary Avidin trapped in a ClyA nanopore, according to an embodiment of the present disclosure.

FIG. 1E is a cross-sectional schematic view of the nanopore 110 of FIG. 1A with a protein 120 sited in the nanopore 110. In the various embodiments, the protein's cross-sectional extent can be greater than the smallest inner diameter of the nanopore; i.e., the protein cross-sectional extent is at least as large as the smallest nanopore diameter along nanopore length. Further, the protein's cross-sectional extent can also be greater than the extent of the inner nanopore diameter at sites along the nanopore length other than the site of the smallest inner diameter.

For example, referring to FIG. 1C, the cross-sectional extent of the protein Avidin is larger than both the smallest ClyA inner diameter, 4.1 nm, and the mid-section diameter of the ClyA nanopore, having an inner diameter of 5.4 nm. Even with this larger radial diameter, an exemplary protein 120 can enter the nanopore 110 by virtue of, e.g., mechanical flexibility in the structure of protein 120. In addition, one or both ends of nanopore 110 can have an inner diameter that is greater than an extent of protein 120 to thereby enable entry of protein 120 at least partially into nanopore 110 if protein 120 cannot otherwise enter nanopore 110. With this arrangement, protein 120 can enter nanopore 110 and snugly fit within nanopore 110 at one or more sites along the length of nanopore 110. This results in match between a nanopore 110 and a protein 120, such as the case for a ClyA nanopore and an Avidin protein.

In some examples, Avidin can be used to build a protein shuttle which can be trapped by a ClyA dodecamer nanopore. For the protein shuttle, Avidin can be configured as the protein 120 that enters nanopore 110, as shown by FIG. 1E. The protein shuttle can have additional molecules attached to the protein shuttle, as shown further with regards to FIG. 1F.

Referring back to FIG. 1E, a cross-sectional extent of protein 120 can be substantially similar in size to an inner lumen diameter of the nanopore 110. For example, the cross-sectional extent can be 5.5 nm and the inner lumen diameter can be 5.4 nm. Avidin-ClyA is an example protein-nanopore pair that demonstrates a radial geometry in which protein 120 has a cross-sectional extent that is at least about the diameter of nanopore 110 or slightly larger than the diameter of nanopore 110 at one or more sites along the nanopore length. Further, the ClyA nanopore includes an inlet diameter of 6.5 nm that is larger than at least the cross-sectional extent of the Avidin protein, whereby the Avidin protein can enter the ClyA nanopore and then snugly fit at a site within the nanopore along the nanopore length.

Additionally, an inner lumen diameter of nanopore 110 can prohibit protein 120 from entering nanopore 110 in certain configurations. For example, Avidin can be oriented so that the fourth dimension the fourth dimension 128 (7.8 nm) enters the inlet of nanopore 110. Avidin's fourth dimension is much larger than the ClyA inlet diameter 114 of FIG. 1A (6.5 nm). If Avidin entered the ClyA nanopore in an orientation where the fourth dimension 128 extends along the inlet diameter 114, then Avidin would not fully enter the ClyA nanopore. Therefore, FIG. 1E shows how a match in dimension between a nanopore diameter and a protein cross-sectional extent can enable docking in a particular orientation and or location at or in the nanopore. In addition, or as an alternative, electrical charges in the nanopore lumen and/or on the protein can enable docking in a particular orientation and/or location at or in the nanopore (not shown).

The fitting of Avidin in a ClyA12 nanopore is a close fit and can create a stable bond. The stable bond enables the study of any target molecule attached to the Avidin. FIG. 1E shows molecular models, with dimensions, of the protein Avidin and of the dodecamer ClyA12 nanopore. The present application leverages this close match between the cross-sectional extent of Avidin and the inner ClyA12 nanopore lumen diameter, for various well-defined Avidin orientations and at various points along the length of the ClyA12 nanopore. As a result, this pair is a particularly viable embodiment as an arrangement for a nanopore-matched protein shuttle as provided herein. In some cases, deglycolitated avidin can be used as a protein shuttle.

Although Avidin with the ClyA nanopore is discussed within the present application, any other protein shuttle and nanopore combination can be used, where the cross-sectional extent of the protein shuttle is at least about the extent of the smallest diameter of the inner lumen of a nanopore. In one example, a smallest diameter of the nanopore lumen is no greater than the cross-sectional extent of a protein shuttle fitted in the nanopore lumen. In another implementation, a protein shuttle with dimensions smaller than the pore lumen diameters can also be used as long as the minimum lumen diameter is smaller than the cross-sectional extent of the protein shuttle and as long as the protein shuttle can be stably trapped at a particular location and with a particular orientation relative to the nanopore.

Figure 1F:
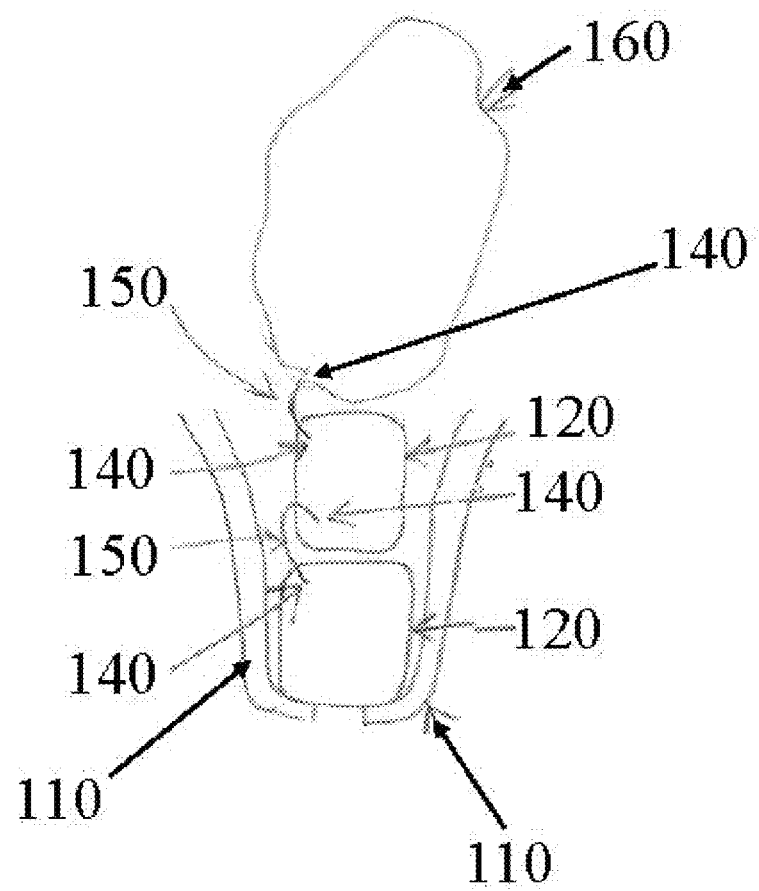
FIG. 1F shows a cutout view of an exemplary protein shuttle trapped in a ClyA nanopore, according to an embodiment of the present disclosure.

FIG. 1F is a cross-sectional schematic view of the nanopore 110 and protein molecule 120 including a target molecule 160 appended to the protein molecule 120 in the nanopore 110 by way of a primary linking species 140 and a secondary linking species 150 which are attached between the target molecule 160 and the protein molecule 120 in the nanopore 110. This protein shuttle enables nanopore-based study of the target molecule 160 by drawing the target molecule 160 to and/or at least partially into the nanopore 110 by means of the protein molecule 120. The protein shuttle can have more or fewer components as shown in FIG. 1F, so long as the protein shuttle has a protein molecule 120.

The primary linking species 140 can connect the protein molecule 120 to the secondary linking species 150. The primary linking species 140 can also connect the secondary linking species 150 to the target molecule 160. In some examples, there can be multiple chains of a protein molecule 120 connected to a primary linking species 140, a secondary linking species 150, a primary linking species 140 and another protein molecule 120. However, more than one protein molecule 120 is not needed.

In some examples, protein molecule 120 can be positively charged and configured to attach to a negatively charged nanopore 110. For example, ClyA is negatively charged along an interior ring.

A judicially chosen protein-pore pair can serve as a platform for the study of protein 120, through deterministic clearing of protein 120 from nanopore 110 with a control voltage, as discussed further below. Referring back to FIG. 1F, there can also be studied a wide range of target molecules 160 and their interaction with analytes in solution (not shown). A target molecule 160 that is linked to the protein shuttle by way of primary 140 or secondary 150 linking species can be drawn to and studied at nanopore 110 by virtue of its linking to the protein shuttle. As explained above, the protein shuttle can be matched to the sizing of a particular nanopore 110. Properties of the protein shuttle, such as electrical charge, can be exploited to attract the protein shuttle to nanopore 110. The nanopore with matched protein shuttle enables studies of both the protein shuttle and target molecule 160. Other molecules can be linked to the protein shuttle or can react with or at the target molecule, and these molecules can be studied via nanopore 110 as well. For example, substrates and products of a reaction catalyzed by target molecule 160 can be studied due to a secure attachment between protein molecule 120 and nanopore 110.

The protein shuttle can have one or more characteristics that enable protein molecule 120 to be driven to and/or driven at least partially into selected nanopore 110 along with a target molecule 160. For example, the protein Avidin has a significant positive electrical charge at the pH of the native environment of most target molecule proteins. As a result, for the study of target molecule proteins, Avidin can be electrophoretically, electro-osmotically, or otherwise be electrically attracted to and drawn into nanopore 110 with target molecule 160 linked to the Avidin in the molecular shuttle configuration for study of target molecule 160 at nanopore 110.

In some examples of the present disclosure, protein molecule 120 can be Avidin and primary linking species 140 can be biotin. FIGS. 1B-1C showed that each beta barrel 123 of Avidin is open at one end. This allows a primary linking species 140 to enter and bind to residues inside beta barrel 123. Referring back to FIG. 1F, biotin can be an exemplary linking species configured to bind to residues inside beta barrels 123 of Avidin. The binding of biotin to Avidin represents the strongest non-covalent ligand bond found in nature, with a dissociation constant of 10-15 M. The strong bonding between the protein Avidin and its ligand biotin can be exploited to enable the attachment of a linking species to Avidin by way of biotin bonding to Avidin, so that target molecule 160 can be configured with secondary linking species 150 in a molecular shuttle arrangement for study of target molecule 160 at nanopore 110. Biotin has strong and specific affinity to Avidin. Biotin can bind in a biotin binding pocket of avidin. Avidin has one binding pocket per monomer. Since Avidin is a tetramer, there are four binding pockets per avidin.

Linking species 140 can include molecules with biotin at one location. For example, the linking species 140 can be a linear molecule that has a number of polyethylene glycol (PEG) units to adjust the length. Biotin can be at one end and maleimide can be at the other. For example, biotin can bind to Avidin on one end. Maleimide can bind to a naturally occurring or an engineered-in cysteine residue on a target molecule 160 at the other. The secondary linking species might not be needed.

The secondary linking species 150 can be provided as, e.g., a polymer molecule, a protein, DNA, Cas9, lysine, a peptide, or other suitable species that can be attached to a target molecule 160. The secondary linking species 150 attached to the Avidin through biotin bonding to the Avidin and secondary linking species. The biotinylation of secondary linking species 150 thereby enables a strong bond between an Avidin-biotin complex and secondary linking species 150. Attachment of secondary linking species 150 to target molecule 160 provides an Avidin-biotin-linking species-target molecule arrangement for study of target molecule 160 by nanopore 110.

In some examples, target molecule 160 can comprise a DNA sequence, an RNA sequence, Cas9, or any other molecule for studying. In some examples, there can be more than one target molecule 160. In some examples, target molecule 160 can be any part of the shuttle, including protein molecule 120 or primary 140 or secondary 150 linking species. For example, a protein shuttle, according to an embodiment of the present disclosure, can be used to shuttle Cas9. Cas9 can be introduced to a primary and or secondary linker and then to Avidin, and subsequently captured by a nanopore. Once the Cas9 is captured, it can be used to do CRISPR analysis.

A protein shuttle can include a number of primary 140 and secondary 150 linking species that are themselves proteins, e.g., neutrAvidin, streptAvidin, or other suitable species, which can be exploited to deterministically orient an attached target molecule 160.

In some examples, target molecule 160 can comprise a DNA sequence, an RNA sequence, Cas9, or any other molecule for studying. In some examples, there can be more than one target molecule 160. In some examples, target molecule 160 can be any part of the shuttle, including protein molecule 120 or primary 140 or secondary 150 linking species.

Given the deterministic orientation of the shuttle (for example avidin) in the nanopore when the shuttle (for example avidin) is captured in its stable trap state (the docked state), the orientation of the target molecule 160 will also be deterministic if the point of linkage to the target protein is known (for example when a cysteine is engineered in to the target protein in a particular residue location) and the length of the linker is chosen appropriately for that target molecule. In some examples, primary 140 and/or secondary 150 linking species can have a form fitting arrangement in nanopore 110. Therefore, primary 140 and/or secondary 150 linking species can orient the protein shuttle in nanopore 110 in a deterministic arrangement that extends to target molecule 160. Thereby, target molecule 160 is provided with a deterministic direction relative to nanopore 110. In one example of such, between one and four Avidin linkers are employed for the tetramer Avidin, given that such as four binding sites for biotin. In this protein shuttle arrangement, only one of the species, e.g., the leading Avidin, needs to provide properties that enable driving of the shuttle to nanopore 110. For example, only the leading Avidin needs to be electrically charged to enable electrophoretic or electroosmotic driving of the shuttle. The linking Avidin species can be neutrAvidin or streptAvidin. Other protein, and other linking species can be employed.

For any of the protein shuttle arrangements described above, there can be shuttled any suitable target molecule 160, including a PSII molecule. PSII is an enzyme that catalyzes the splitting of water molecules, into four protons, four electrons, and one oxygen molecule per two water molecules. The conformational dynamics and changes during the four-step catalytic process can be studied. The process is driven by sunlight (photons) so in this case the reagents (substrates) for the enzymatic process are two water molecules and 4 photons, and the products are four protons, four electrons, and one oxygen molecule.

The shuttle protein can be stably linked to target molecule 160. The linking species 140 can be specific to particular location(s) on the protein molecule 120 and on the target molecule 160. The linking species 140 can have a variable length to match the needs for a specific target molecule. For example, with respect to PEG units, the length of the linking species 140 is adjusted with the number of PEG units between biotin and maleimide. The protein molecule 120 can be linked to a broad class of important target molecules 160. Proteins, including enzymes, can be linked as target molecules 160 with appropriate linkers, for example the biotin-PEG units-maleimide linker.

Any suitable molecule can be studied as the target molecule.

Figure 2A:
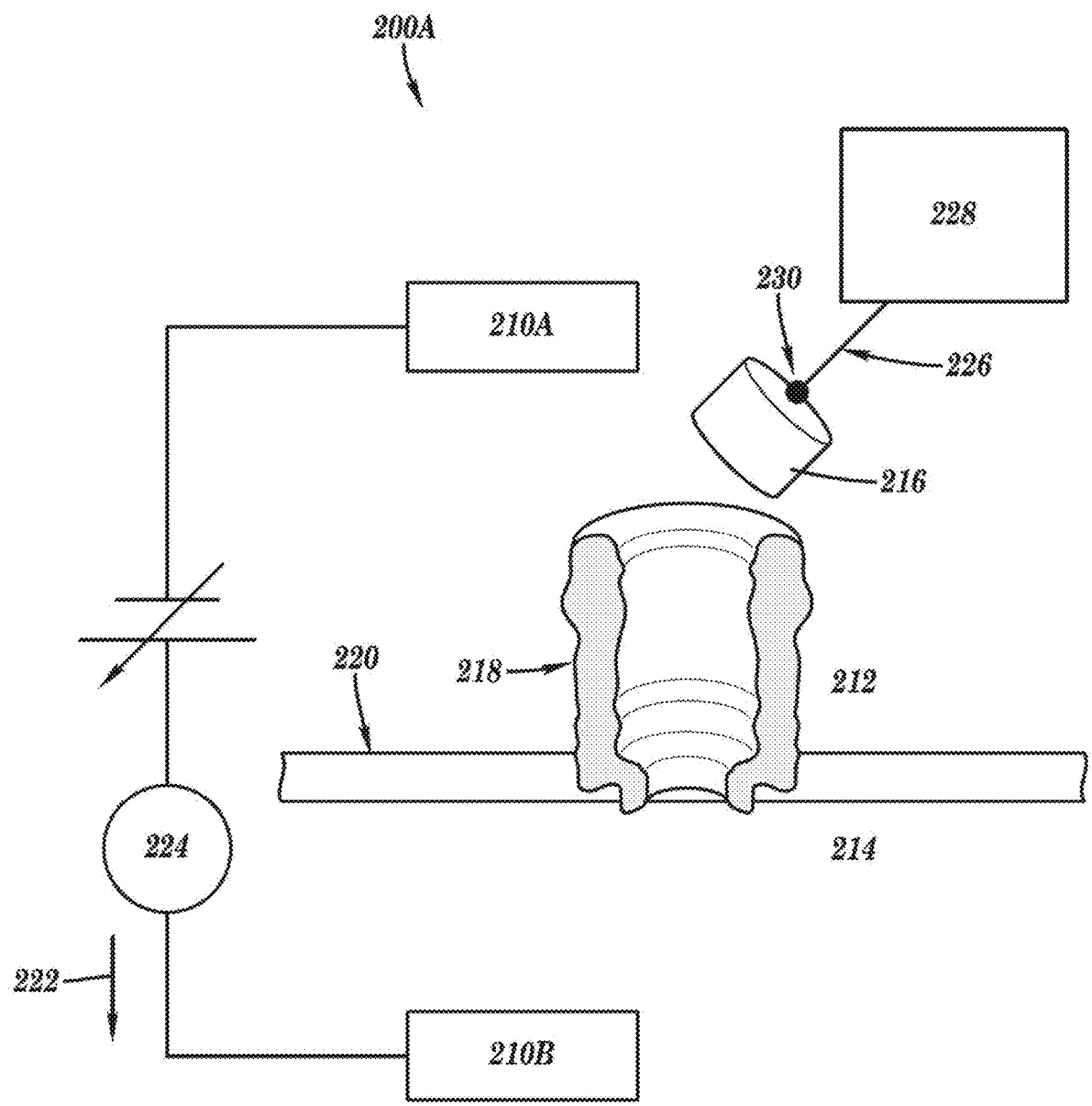
FIG. 2A shows an exemplary nanopore sensor system, according to an embodiment of the present disclosure.

FIG. 2A shows an exemplary nanopore sensor system 200A, according to an embodiment of the present disclosure. The nanopore sensor system 200A can include a first electrode 210A, a second electrode 210B, a first fluidic chamber 212, a second fluidic chamber 214, a protein molecule 216, a nanopore 218, support structure 220, a current 222, a current sensor 224, a linking species 226, a target molecule 228, and biotin 230. Although not shown in FIG. 2A, system 200A can include a flushing system whereby molecules can be flushed on demand separately from the first and second fluidic chamber. In some cases, this system can also be used to inject molecules into the first and or second fluidic chamber.

The first electrode 210A can be disposed in the first fluidic chamber 212. The second electrode 210B can be disposed in the second fluidic chamber 214. Electrodes 210A, 210B can be configured to apply a voltage between chambers 212, 214. Fluidic chambers 212, 214 can have fluids in them. For example, second fluidic chamber 214 can have a fluid with a negative voltage relative to a fluid in first fluidic chamber 212. The support structure 220 can comprise a lipid bilayer or other material configured to trigger fluidically separate chambers 212, 214.

An applied voltage bias polarity can generate a current 222 which can be set based on the electrical charge of a selected protein 216 to cause the protein to be electrically driven into nanopore 218 from one of the chambers. For example, for drawing Avidin into a nanopore, second fluidic chamber 214 is kept at negative voltage relative to first fluidic chamber 212, and Avidin is provided in first fluidic chamber 212. Therefore, characteristics of protein shuttle 216, e.g., electrical charge and or electric dipole moment, enable voltage-controlled docking, undocking, capture, and uncapture of protein shuttle 216.

After docking of just the charged protein 216 (avidin for example, more generally the shuttle without target protein,) in or at the pore, there can be non-zero residual current through the pore and that residual current should have low noise background. For example, the root-mean-square current noise for a 1 kHz bandwidth can be 10% or less of the residual current. An Avidin dimer or an avidin monomer can also be used as a shuttle in combination with a nanopore, for example, the nanopore can be ClyA or *Mycobacterium smegmatis* porin A (MSPA).

Turning to further specifics of the system 200A, a nanopore 218 can be provided in support structure 220 in any suitable manner. For example, ClyA nanopores can be provided in a lipid bilayer by adding ClyA to first fluidic chamber 212 of the system 200A. When a single one of the ClyA nanopores inserts itself into the membrane, as shown in 200A, then ionic current 222 measured in current sensor 224 of 200A increases due to ionic current flow through the nanopore between the two chambers of solution. Once nanopore 218 is in place in support structure 220, protein 216, or protein-based molecular shuttle can be electrophoretically or otherwise driven into nanopore 218. Prior to this step, nanopores remaining in solution can be flushed from first fluidic chamber 212.

In some examples of the present disclosure, the nanopore sensor system 200A can include particular components. The support structure 220 can be a lipid bilayer membrane suspended across a 40 micrometer Teflon frame in an electrolytic buffer solution (150 mM NaCl, 15 mM TRIS pH 7.5). A silver/silver-chloride electrode 210A, 210B can be placed in each reservoir and a current 222 of a few tens of mV can be applied across the membrane. The membrane electrically isolates the two reservoirs, and initially no current 222 flows between the electrodes 210A and 210B. Preformed ClyA pores can be added to the first fluidic chamber 212, and when a single pore 110 inserts in the membrane—observed as a step change in current to a stable open-pore current—the first fluidic chamber 212 is immediately flushed with buffer electrolyte solution to prevent additional ClyA pores from inserting into the membrane. Once a single pore is in place in the membrane, 10 pmol of Avidin can be added to the first fluidic chamber 212. The current 222 is transiently blocked when individual, positively charged Avidin molecules are trapped by and subsequently escape or are ejected from the nanopore 218.

The ionic conductance through an individual voltage-biased nanopore 218 can be measured and analyzed prior to protein 216 insertion in the first fluidic chamber 212. For the exemplary ClyA nanopore, a conductance of 1.66 nS, measured at a 30 mV bias, is found to be common and can be employed for the capture of Avidin. ClyA nanopores with a conductance within a percent of this value are the most common ones observed as inserting in a membrane and are the most stable over time.

In one example of a method for driving a protein into a nanopore, Avidin is inserted in a ClyA nanopore. For example, after 10 pmol (1 microliter volume) of Avidin is added to the 250 microliter first fluidic chamber 212 of 200A with a 1.66 nS ClyA nanopore in place on a lipid bilayer, the current through the −35 mV voltage-biased nanopore is observed to transiently drop from an open-nanopore value of about 58 pA as individual Avidin protein molecules are captured by, and escape from, the nanopore 218. In some cases a permanent trap state of avidin in ClyA can be observed: this can be referred to as the docking state of the shuttle protein avidin in ClyA. For measuring current 222 there can be employed any suitable current sensor 224, e.g., a Molecular Devices Axopatch patch clamp amplifier. The output signal can be processed, e.g., by a 10 kHz, 4 pole Bessel filter, to minimize high frequency current noise, and then sampled and digitized, and stored, for processing.

The linking species 226 can be connected to the protein molecule 216 and the target molecule 228 via biotin 230. The target molecule 228 can be a PSII target molecule.

The Avidin that is inserted into a nanopore 218 in system 200A can be arranged as a protein shuttle, including one or more linking species 226 and target molecules 228. The protein molecule 216 and target molecule 228 in the chambers 212 and 214 of a nanopore system 200A, the Avidin or other lead protein can be drawn to and trapped in the nanopore 218, e.g., the ClyA nanopore, from the first fluidic chamber 212.

The shuttle structure with protein molecule, target molecule, and linker(s) can also be pre-formed before injection of the shuttle structure units into first or second fluidic chamber.

In an alternative configuration, the Avidin, or other leading structure of the shuttle, is disposed in one of the two fluidic chambers, e.g., first fluidic chamber 212, and target molecule is disposed in the opposite of the two fluidic chambers, e.g., second fluidic chamber 214. The target molecule 228 here can be, e.g., biotinylated, with linking species 226 and biotin 230 at the end of linking species 226 opposite target molecule 228. The target molecule 228 can arrive at nanopore 218 from second fluidic chamber 214, and link to protein 216 that is already trapped in nanopore 218, through an outlet of the nanopore to second fluidic chamber 214. After this linking has occurred, the voltage or other stimulus for driving protein 216 to nanopore 218 can be adjusted, e.g., to lessen the trapping of protein 216, drawing protein 216 back toward first fluidic chamber 212 and thereby pulling target molecule 228 further to nanopore 218 from second fluidic chamber 214, via linking species 226 that is attached between protein 216 and target molecule 228.

System 200A thus can provide for electrophoretic driving and capture of Avidin 216 and correspondingly, of a molecular shuttle including of an Avidin-biotin+linking species+ target molecule arrangement, into a nanopore 218. System 200A provides for deterministic control of an Avidin protein shuttle attached via biotin 230 and a linking species 226 to a target molecule 228, here a PSII photosynthetic enzyme, for controllable direction and orientation of the PSII target molecule 228 toward and at least partially into the nanopore.

Protein molecule 216 can be trapped in nanopore 218 and target molecule 228 can partially enter nanopore 218 from first fluidic chamber 212. The capture of protein molecule 216 by nanopore 218 in the docking state and with the target molecule linked to the protein molecule can be considered a blockage event. A change in current signal in this situation from the current signal when the protein molecule 216 alone is docked, when the same applied voltage between the fluidic chambers is applied in the two cases, is the current signal that is of interest and contains the signals corresponding to target molecule sensing with the sensor platform. In some examples of the present disclosure, target molecule 228 can be disposed in the second fluidic chamber 214 and can be captured by nanopore 218 such that target molecule 228 at least partially obstructs the at least one nanopore during a blockage event (not shown).

FIG. 2A shows a nanopore system 200A where a protein 216 such as Avidin that is provided in first fluidic chamber 212 can be electrophoretically, electro-osmotically, or otherwise driven to nanopore 218, at least partially taken into nanopore 218, held at nanopore 218 for a selected duration of time, and then subsequently released from nanopore 218 back into first fluidic chamber 212. The released protein 216 can then be re-drawn to and re-trapped in nanopore 218. Alternatively, a different protein from first fluidic chamber 212, or from second fluidic chamber 214, can be driven to nanopore 218 for trapping. When arranged in a molecular shuttle, the Avidin thereby can be controlled as the engine that moves the shuttle toward, into, and out of nanopore 218. Thereby, target molecule 228 linked to protein 216 can be captured at nanopore 218, for a controlled capture time, to enable evaluation of linked target molecule 228, even at the single molecule level. Depending on the size of target molecule 228, target molecule 228 can be pulled fully into nanopore 218 with Avidin, or as shown here, can be pulled partially into nanopore 218. Target molecule 228 alternatively can be pulled to the entrance of nanopore 218. The understanding of the unperturbed electronic properties of the Avidin-ClyA nanopore platform as well as the biotin-Avidin-ClyA system provided herein enable such target molecule capture and evaluation.

A matched pair of a nanopore and a charged protein shuttle can cause the shuttle protein to dock in a particular and reproducible orientation at or in the nanopore. For example, a ClyA dodecamer can be matched with Avidin tetramer. This combination is ideal for a broad range of pH values. A shape form fit can be used to ensure that the charged protein shuttle docks in the pore at a particular location and with a particular orientation relative to the pore.

For example, Avidin can be caused to dock in at a particular orientation leading to a blocking of a current through the nanopore. An applied voltage can cause the protein shuttle to be controllably docked and undocked.

FIG. 2A demonstrates the operation of the protein shuttle, here a shuttle including an Avidin-biotin+linking species+ target molecule arrangement, for controllably directing a target molecule to and perhaps into a nanopore. System 200A allows for trapping, in or at the nanopore, molecules of interest that have low or no net charge, and for trapping molecules of interest with controlled orientation relative to the nanopore.

Figure 2B:
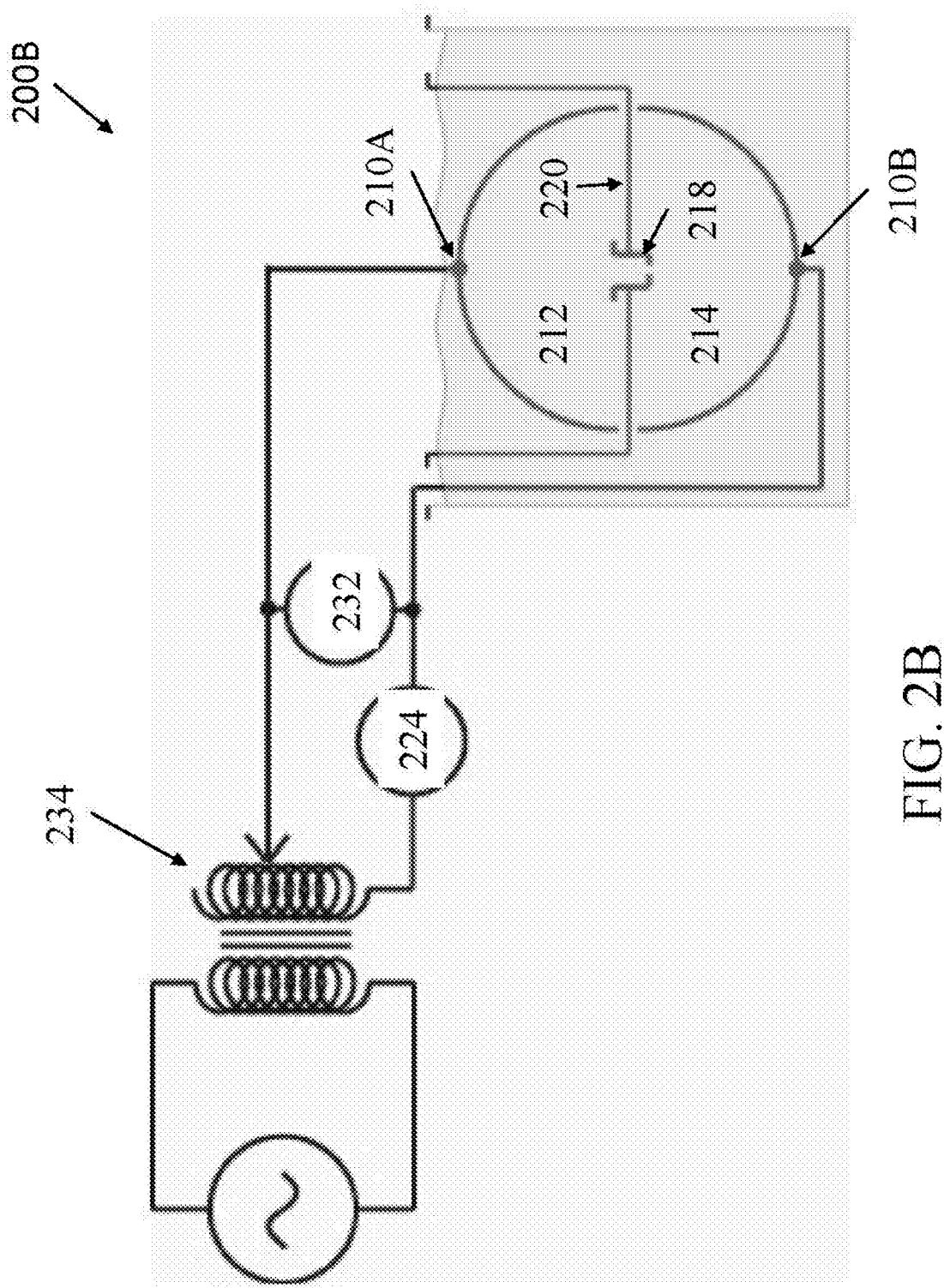
FIG. 2B shows an exemplary set-up for measuring the geometric contribution to nanopore conductance, according to a scaled up macroscopic version of the nanopore structure, for example with a 3D printed nanopore in plastic material.

FIG. 2B shows an exemplary macroscopic nanopore sensor set-up 200B for measuring nanopore conductance, according to an embodiment of the present disclosure. FIG. 2B includes many of the same components as FIG. 2A and further comprises a voltmeter 232, and a transformer 234. Therefore, the nanopore sensor set-up 200B can measure ionic current flow through nanopore 218 between first fluidic chamber 212 and second fluidic chamber 214.

For example, a macroscopic nanopore 218 can be glued into a thin insulating plastic sheet to simulate the lipid membrane. The sheet can separate two reservoirs of 150 mM NaCl in water, and in each reservoir hemispherical electrodes 210A and 210B of 11.4 cm radius surrounded the pore. Conductance measurements on the macroscopic pore system 200B can be made with a range of 60 Hz AC voltages from 10-50 volts rms. Conductance can be calculated from a linear slope of the I-V plot. No phase shifts between observed currents and applied voltages should be observed. A temperature of the electrolyte can be monitored and measurements can be restricted to a few seconds in duration to minimize electrolyte Joule heating.

Scaling the measured conductance value by $3/107$ obtains the geometrical conductance for nanopore 218 at 2.87 nS. The inverse of the measured geometric pore conductance is a sum of the inverse conductance for the pore alone, and the access resistance. The correction of access resistance to infinite electrode radius can increase the total resistance by 1.57 percent. This measured and scaled conductance value will be significantly reduced by exclusion of part of the chlorine ions' contribution to the pore conductance. To evaluate the reduction factor, a 1.66 nS ClyA nanopore can be captured in a lipid bilayer membrane with a 150 mM buffered salt solution on both sides. First fluidic chamber 212 can be refilled with a 20 mM buffered salt solution. This can create a measurable open circuit potential of 26 mV across nanopore 218 due to an unequal transfer of sodium versus chlorine ions across the pore in the drift-diffusion process.

The Goldman-Hodgkin-Katz (GHK) flux equation from ion-channel biophysics can analyze the measured open circuit potential across the pore. The GHK equation can calculate the permeability factor reflecting the extent to which the chloride ions are blocked, relative to the sodium ions, from passing through nanopore 218. Negative charges in the lumen close to the outlet aperture can repel negative chloride ions in the NaCl-salt solution and result in a reduced mobility and diffusion constant for chloride ions passing through the pore. By applying a salt gradient across the pore, this difference in mobility and diffusion constant can cause a voltage across the pore to build up. By measuring this voltage in steady state, i.e., when there is no current through the pore, the GHK equation can deduce the ratio of the mobilities of chloride and sodium ions, and thereby deduce the relative charge exclusion for chloride ions by the pore.

The GHK calculation results in a permeability factor of 0.22, which is smaller than the 0.33 obtained at higher molarities. A larger chlorine ion blockage effect should be expected in the macroscopic set-up 200B due to a larger Debye screening length at lower ionic strength. The obtained permeability factor reduces nanopore conductance from the geometrical pore conductance value. This analysis can help predict a ClyA12 pore conductance under the conditions of the system shown in FIG. 2A, where the pore conductance should therefore be 1.75 nS.

Simple scaling arguments show that the conductance prediction for the other possible oligo candidate, the slightly larger 13'mer, would be 1.97 nS, which rules it out. A higher conductance shows that the nanopore is not a good fit for the protein molecule. For example, the 13'mer pore's larger size (diameter) no longer makes it a formfitting pore for Avidin so Avidin does not dock in the 13'mer pore in a particular location and with a particular orientation. A small number of pores exist with 1.9 nS, but these pores are somewhat unstable when inserted in membrane 220. Therefore, FIG. 2B shows an exemplary macroscopic system 200B which can identify constraints for appropriate microscopic systems (for example, the system of FIG. 2A).

Figure 3A:
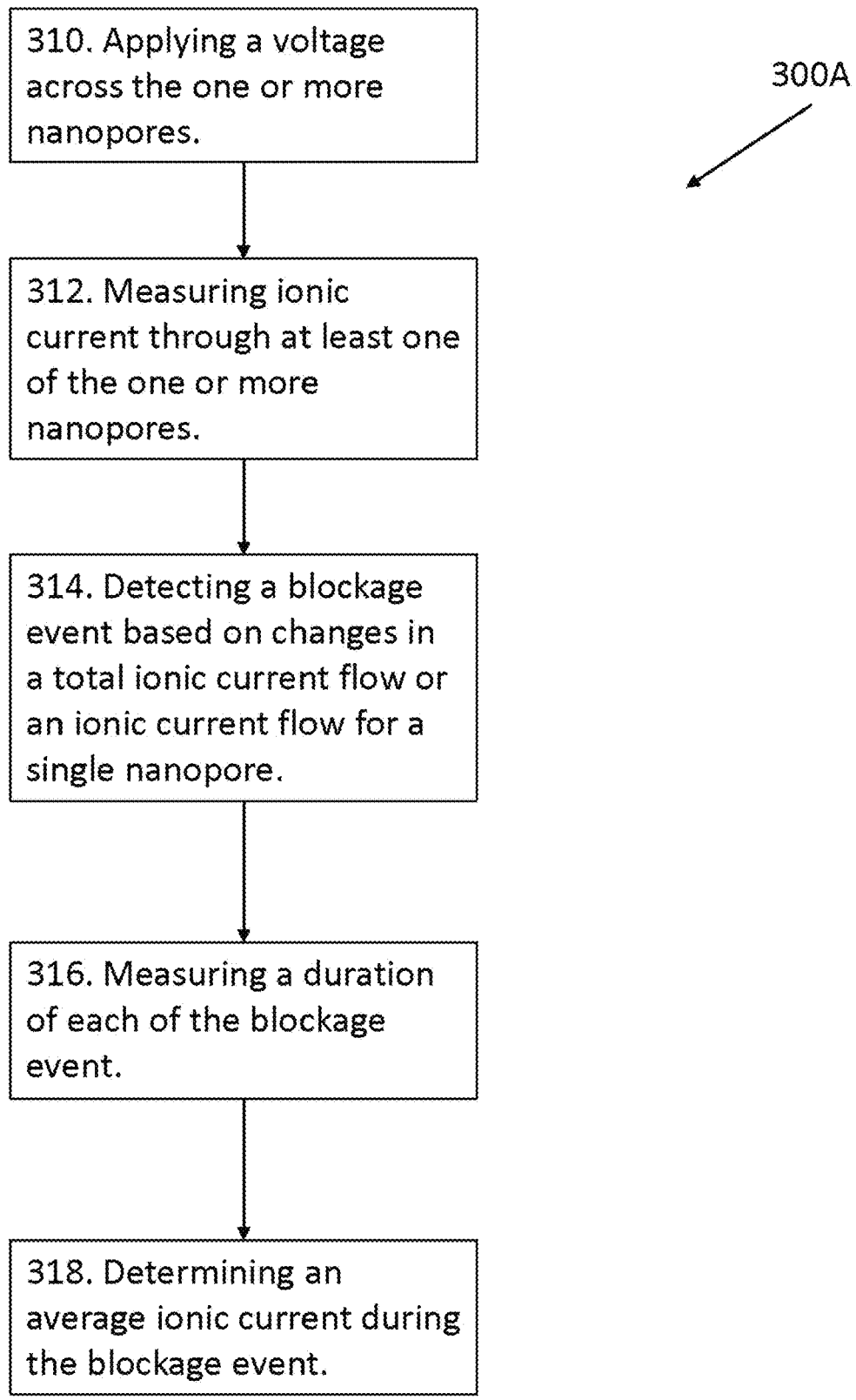
FIG. 3A shows an exemplary methodology for using a nanopore sensor, according to an embodiment of the present disclosure.

FIG. 3A shows an exemplary methodology 300A for using a nanopore sensor, according to an embodiment of the present disclosure. The exemplary methodology 300A can use a nanopore sensor as described with respect to FIGS. 2A-2B. The methodology 300A can provide a method of analyzing molecular trapping in and or at one or more nanopores.

The method can begin at step 310 by applying a voltage across the one or more nanopores. The voltage can draw at least one protein shuttle towards at least one of the one or more nanopores. The protein shuttle can comprise an electrically charged protein molecule. In some instances, the protein shuttle can further comprise one or more linking species, and a target molecule. While applying the voltage, the method can provide for measuring an ionic current through at least one of the one or more nanopores in step 312.

While measuring the ionic current, the method can further provide for detecting a blockage event in step 314 based on the ionic current for at least one of the one or more nanopores. A blockage event indicates a capture of the protein shuttle by at least one of the one or more nanopores. A blockage event can be detected through a change in a total ionic current flow or a change in an ionic current flow for a particular one of the one or more nanopores. The change in the ionic current flow can comprise a decrease in the ionic current flow.

In some examples of step 314, the methodology can optionally include maintaining a voltage after a blockage event had occurred. In other examples, step 314 can include reducing the voltage after a blockage event has occurred. In other examples, step 314 can include increasing the voltage after a blockage event has occurred. In other examples, 314 can include reversing a voltage after a blockage event has occurred.

After detecting a blockage event, the methodology 300A can proceed to step 316, where a duration is measured for the blockage event. After measuring the duration, the methodology can further comprise determining an average ionic current during a blockage event 318.

In some examples, the method 300A can comprise inducing an ejection of the captured protein shuttle by reversing a polarity of the voltage. For example, the method 300A can comprise automatically reversing the voltage after some selected duration. For example, the duration can be one second of measured current blockage. This voltage polarity reversal ejects the positively-charged protein from the nanopore. The voltage bias can then be returned to a negative value, after which the open-nanopore current is again observed, followed by new current blockage capture events. If the protein shuttle with attached target molecule was originally provided in the first fluidic chamber, then the shuttle and target molecule are sent back to the first fluidic chamber. In some cases, by increasing the voltage after the shuttle is trapped, the shuttle can be ejected into the second fluidic chamber even though it originally entered the pore from the first fluidic chamber.

This method can be used for one or more nanopores, for one or more protein shuttles, and/or for one or more blockage events. Therefore, the methodology 300A provides the means to determine whether a protein shuttle was trapped by a nanopore, according to the example shown in FIG. 2C, for example.

Figure 3B:
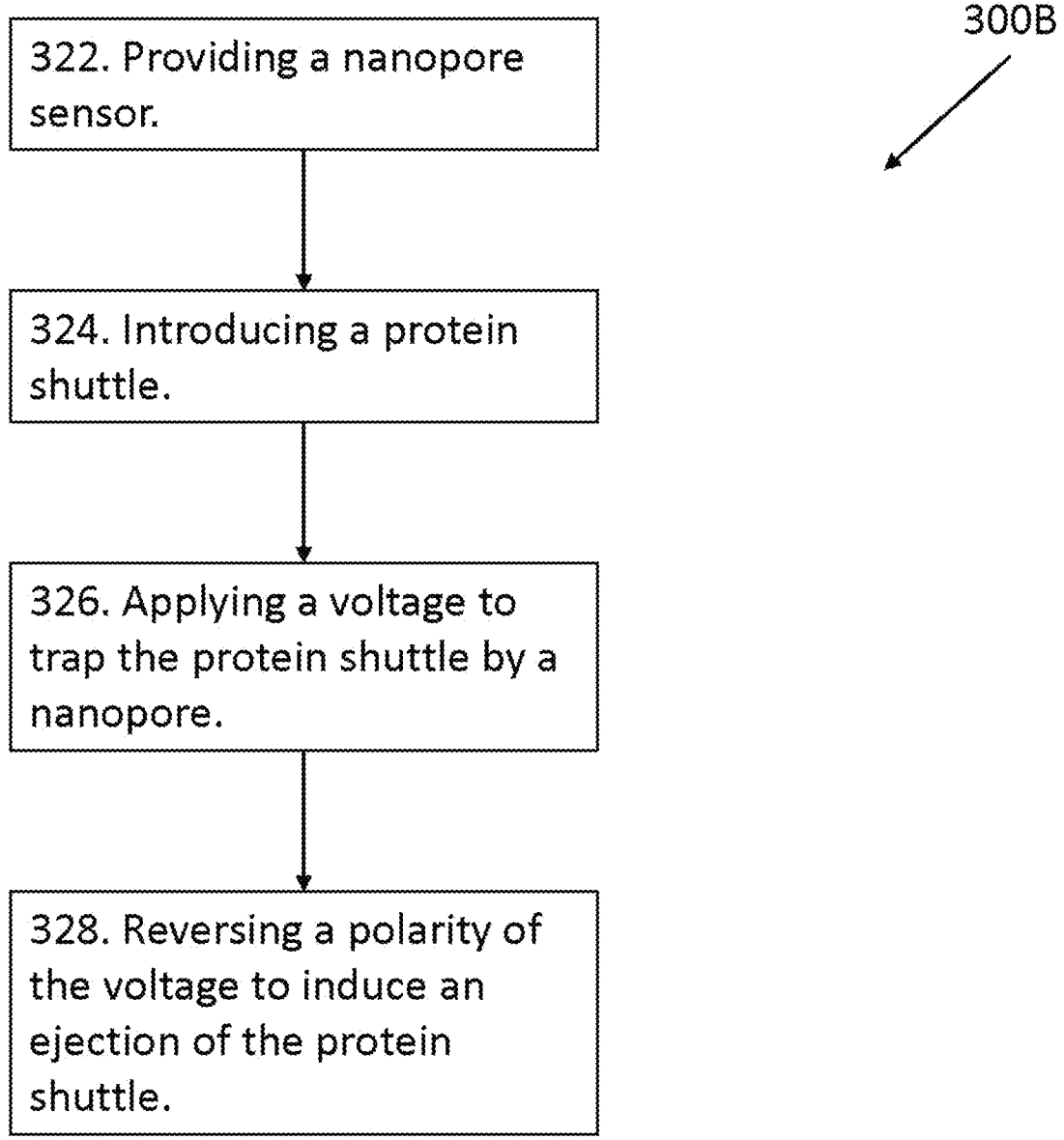
FIG. 3B shows an exemplary methodology for trapping and releasing a protein shuttle, according to an embodiment of the present disclosure.

FIG. 3B shows an exemplary methodology 300B for trapping and releasing a protein shuttle, according to an embodiment of the present disclosure. The exemplary methodology 300B comprises providing a nanopore sensor at step 322. The nanopore sensor can be according to the embodiments of the present disclosure discussed with respect to FIGS. 2A-2C.

Referring back to FIG. 3B, the method 300B can then comprise introducing a protein shuttle at step 324. The protein shuttle can be a protein shuttle as discussed with respect to FIGS. 1F and 2A. The protein shuttle can be introduced into a first fluidic chamber of the nanopore sensor. In some examples of the present disclosure, the protein shuttle can be introduced into a second fluidic chamber of the nanopore sensor.

The method 300B can then comprise applying a voltage to trap the protein shuttle by a nanopore in step 326. In step 328, the method can provide for inducing an ejection of the protein shuttle from the at least one nanopore by reversing a polarity of the voltage.

Therefore, FIG. 3B provides a methodology 300B for capturing and releasing a protein shuttle, according to an embodiment of the present disclosure.

Figure 4:
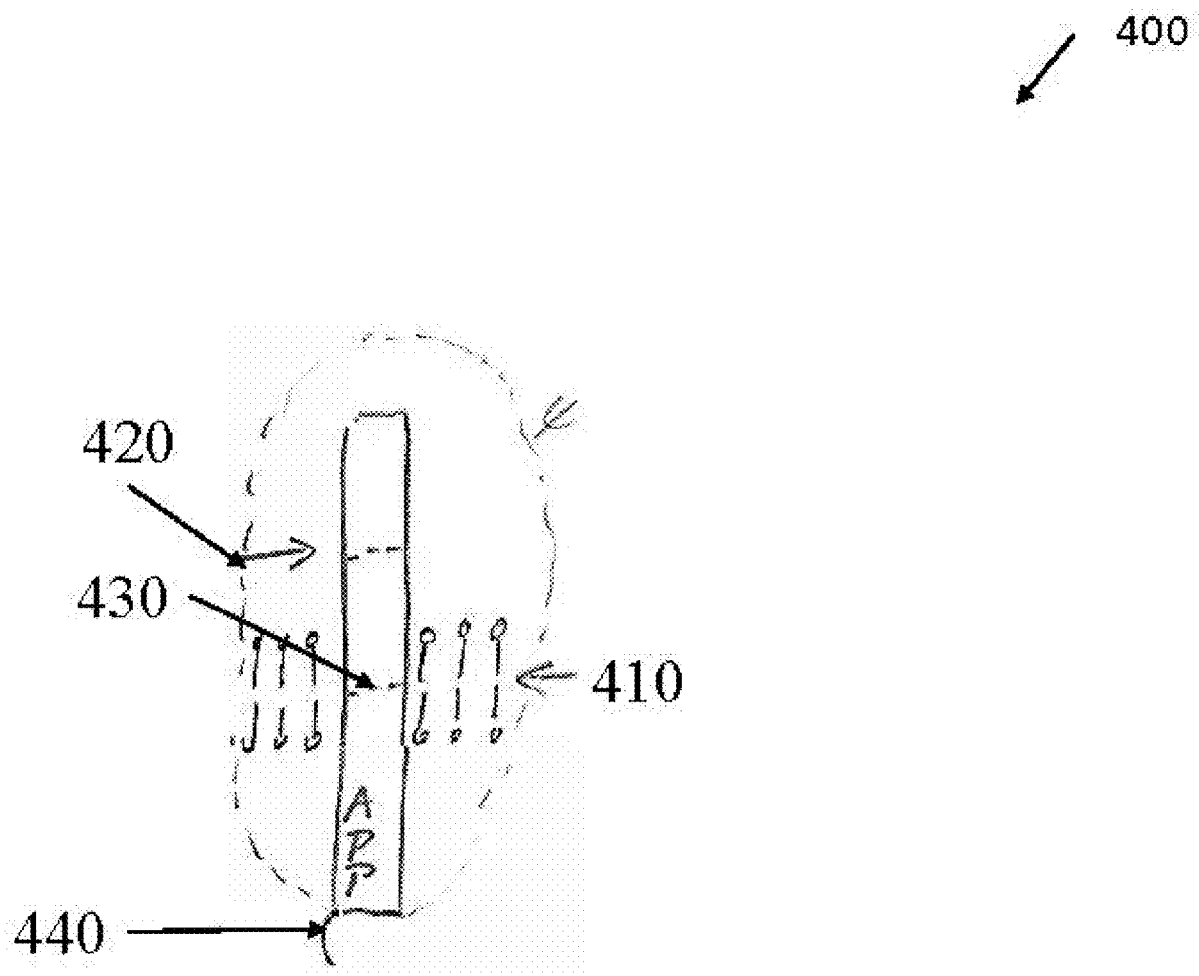
FIG. 4 shows the structure of an exemplary target molecule according to an embodiment of the present disclosure.

FIG. 4 shows the structure of an exemplary target molecule 400 according to an embodiment of the present disclosure. The exemplary target molecule can include lipids or detergent molecules 410; a beta-secretase cleavage site 420; a gamma-secretase cleavage site 430; and a linker molecule 440. In some examples, the target protein can be APP, a membrane-bound protein. The beta-secretase can bind to and cleave the APP protein. The linker molecule can link to a protein molecule, such as Avidin. The cleavage enzymes, β-secretase and γ-secretase can sequentially bind to and cleave the APP protein. By trapping the shuttle with the linked APP protein in the ClyA nanopore, β-secretase and/or γ-secretase can be added to the fluidic chamber of a nanopore sensor. The resulting time-dependent current signals can be monitored to examine the dynamics of the enzymes binding to and cleaving the APP protein. Therefore, for example, a system using this sort of exemplary target can probe whether the dynamics of the nanopore sensor system are changed with targeted drugs aimed at inhibiting the cleavage activity of β-secretase or γ-secretase. The APP cutting by β-secretase and γ-secretase is believed to be of importance for Alzheimer's disease as the cleaving of APP by these enzymes leads to formation of cleavage fragments Aβ that will form β-Amyloid plaques. APP is β-amyloid precursor protein. Aβ is amyloid β-peptide). γ-secretase includes catalytically competent γ-secretase (for example PS1 containing competent γ-secretase complex) and soluble γ-secretase (for example with detergent enzyme solubilization) including soluble competent γ-secretase. β-secretase includes soluble β-secretase. In FIG. 4 the linker is schematically shown to be linked to the APP protein in one location. Dependent on the linker position—for example the linker can also be linked to the opposite end of APP—the platform can be chosen for maximum sensitivity to cleaving of APP by β-secretase and/or γ-secretase.

Any suitable target molecule can be studied at a nanopore platform using a protein shuttle, e.g., an amyloid precursor protein (APP) with lipids or detergent molecules. FIG. 4 shows an example of a target protein 400 structure to be probed, namely, an APP protein, which is a membrane-bound protein, in lipid or with detergent molecules. This protein can be arranged with the protein shuttle for study of the protein at a nanopore. For example, the dynamics of the workings of cutting enzymes such as beta or gamma secretase, and the effect of drug targets on the system, can be studied with the aid of the nanopore-matched protein shuttle, and the shuttle can include any number of linking species as described above.

Figure 5B:
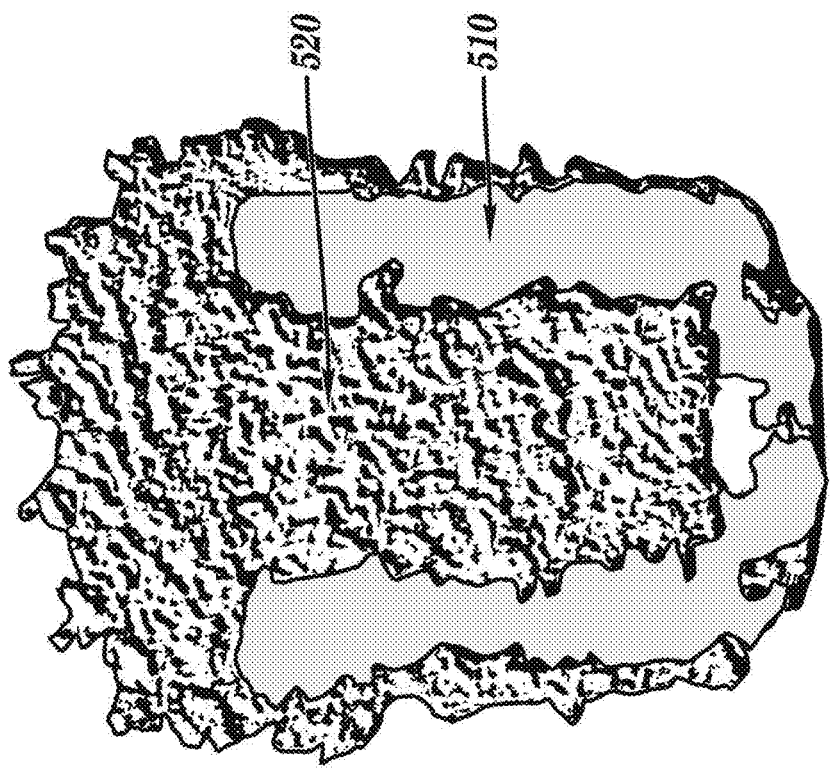
FIGS. 5A-5B show an exemplary nanopore and protein molecule structure, according to an embodiment of the present disclosure.
Figure 5A:
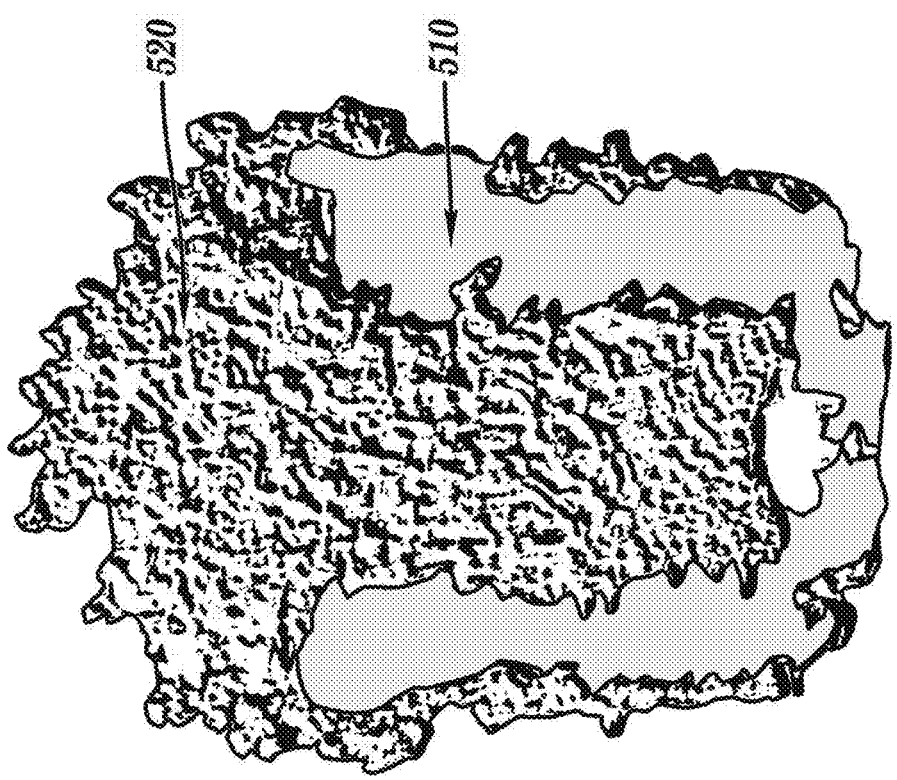

FIGS. 5A-5B show an exemplary macroscopic nanopore 510 and protein molecule structure 520, according to an embodiment of the present disclosure. FIGS. 5A-5B show 3D printed macroscopic models. FIG. 5A shows an Avidin-nanopore configuration wherein a rigid Avidin molecule 520 sits atop a rigid ClyA12 pore 510 oriented to obtain maximum current blockage of 10% in macroscopic conductivity experiment. FIG. 5B shows an elastic Avidin model 520 maximally pressed into rigid ClyA12 pore model 510 achieving 20% blockage in macroscopic conductivity experiment. Scale bar corresponds to 3 nanometers for actual protein and nanopore size.

The nature of the Avidin-ClyA interaction described above for a 1.66 nS ClyA nanopore can be understood on a molecular level if the number of protomers in the ClyA oligomer is known. To address this issue, an experimental methodology can determine which oligo is expected to have the observed conductance of 1.66 nS. There are two phenomena that determine the conductance. One is simply the geometry of the nanopore. This geometric-based conductance is then modified by the presence of charged amino acids on the walls of the nanopore. In fact, in ClyA the limiting site of smallest diameter along nanopore length is known to have a highly negative charge that can block chlorine ion conductance through the nanopore. Geometric and charge selectivity effects can be determined in different experiments and assembled to predict the total conductance of a given nanopore.

To determine the geometrical contribution to the nanopore conductance there can be constructed a model, e.g., 3D-printed model, of a selected nanopore, such as ClyA, scaled up by a factor of 107/3 to atomic coordinates for the ClyA nanopore, as-obtained from the protein database. The 3D printer used to prepare the scaled-up nanopore was a FormLabs Form 2 model, with a resolution of ~50 microns. The dimensions of the molecules were scaled up by a factor of 107/3 from the PDB database. The plastic used for the rigid models was FormLabs Clear (Part #FLPGCL02, FLPGCL03).

To model a protein 520 fitted in a nanopore 510 as provided herein, a 3D-printed Avidin protein 520 can be prepared with the same scaling as used for the ClyA12 3D-printed nanopore 510. The 3D printing plastic used for the flexible Avidin model was FormLabs Flexible (Part #FLFLGR02) with a Shore Hardness of 80A.

Regardless of orientation, the 3D-printed protein 510 was slightly too large to completely enter the 3D-printed ClyA nanopore lumen, mostly being blocked from entry by a few residues on the outside surface of the Avidin 520. Placing the molecule on the rim of the pore 510 in the macroscopic conductance experiment, as shown in FIG. 3A, only reduces the conductance by 10%. With Avidin 520 deeply inserted in the lumen of the pore a shown in FIG. 5B, only a 20% conductance reduction was observed.

Geometrically, elasticity of the protein and/or the nanopore can allow a protein to enter into a nanopore more deeply and with more intimate contact under the force provided by the electric field from the applied voltage bias. In addition, electrostatic charges in a nanopore lumen can interact strongly with electrostatic charges on a protein at short distance when the protein 520 is near the bottom of the nanopore 510. And ionic charge-selectivity effects for conductance may become more intense when a protein 520 is in a nanopore 510, also leading to deeper current blockades. Based on these considerations, it is thereby preferred that a selected protein 520 have a radial diameter that is at least about the same inner lumen diameter of a nanopore 510 in which the protein 520 is to be fitted.

Figure 6A:
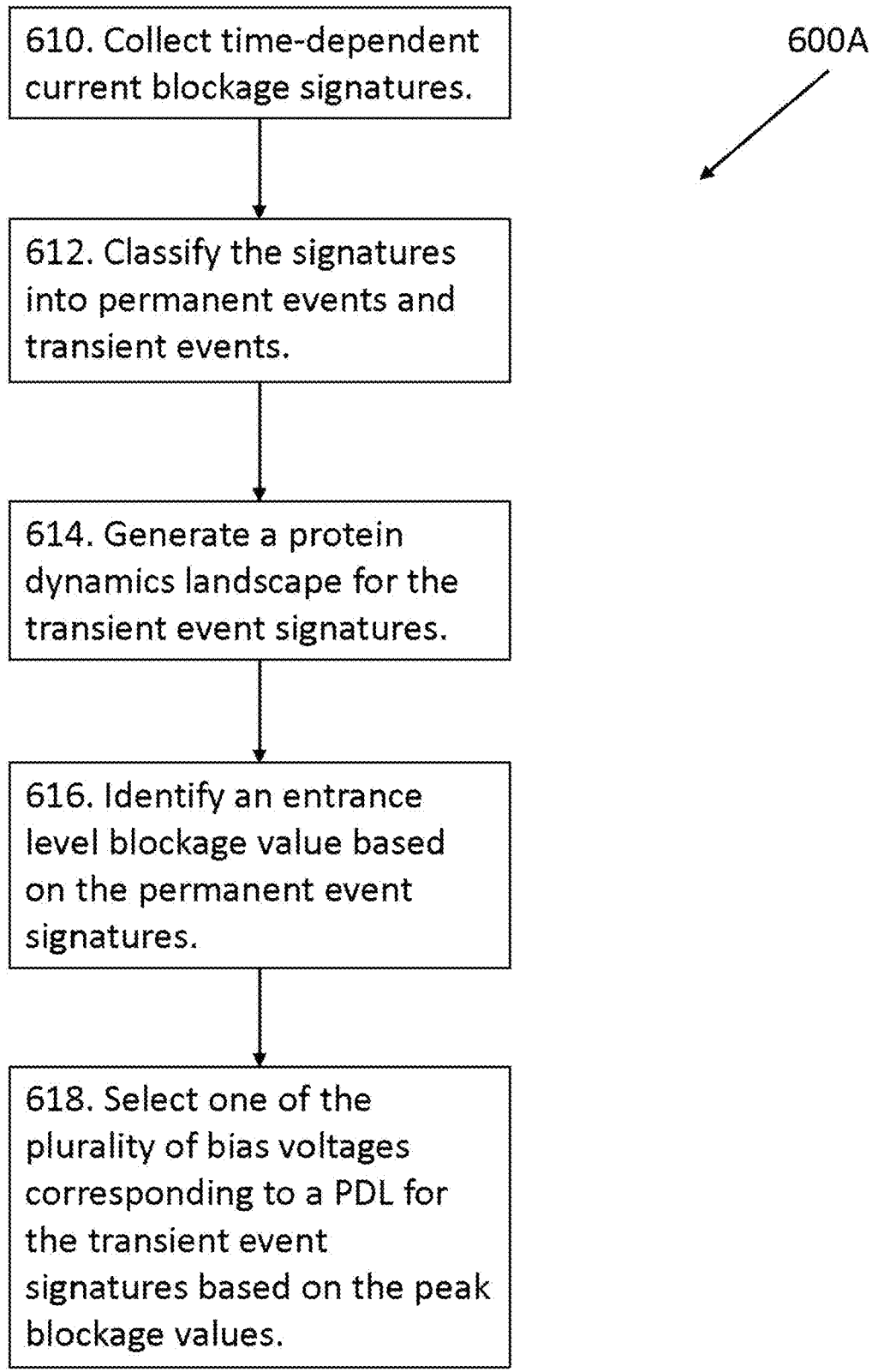
FIG. 6A shows an exemplary methodology for characterizing shuttle capture in a nanopore sensor.
Figure 6B:
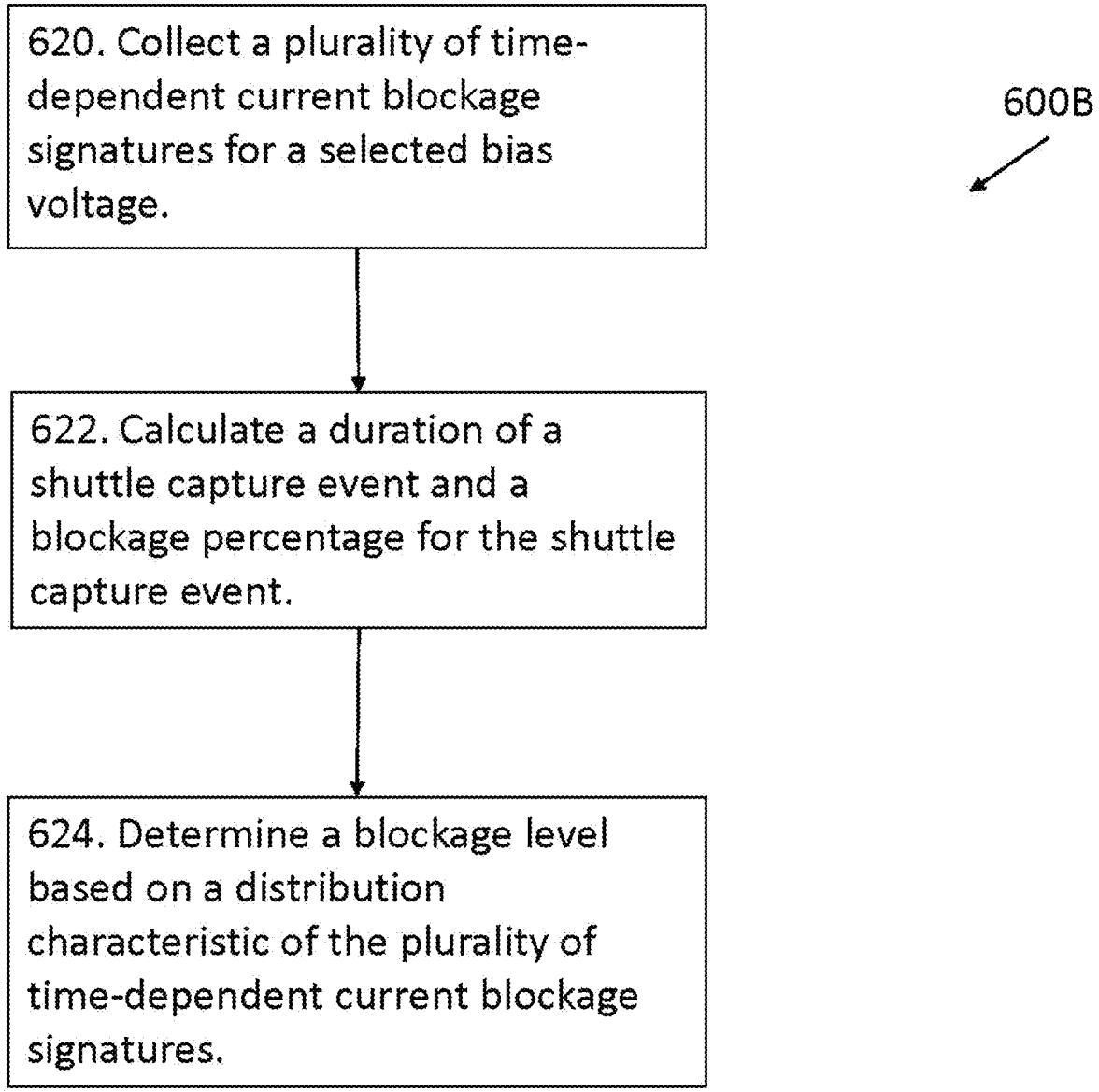
FIG. 6B shows an exemplary methodology for determining blockage levels of at least one nanopore in the nanopore sensor.
Figure 7A:
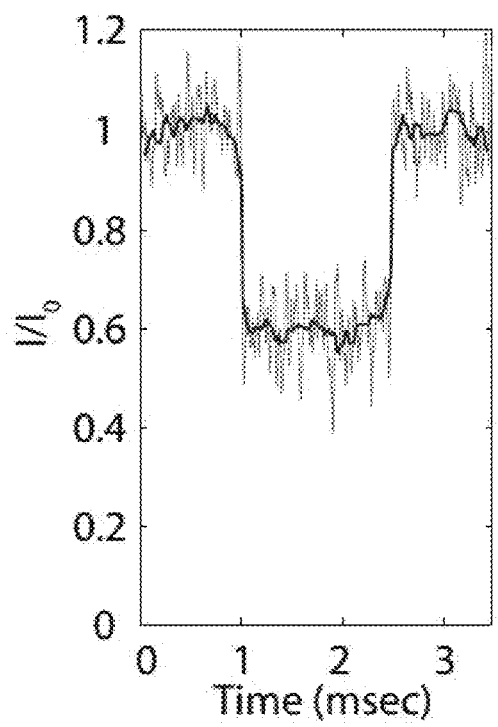
FIG. 7A-7E show exemplary time-dependent current blockage signatures for transient events, according to an embodiment of the present disclosure.
Figure 7B:
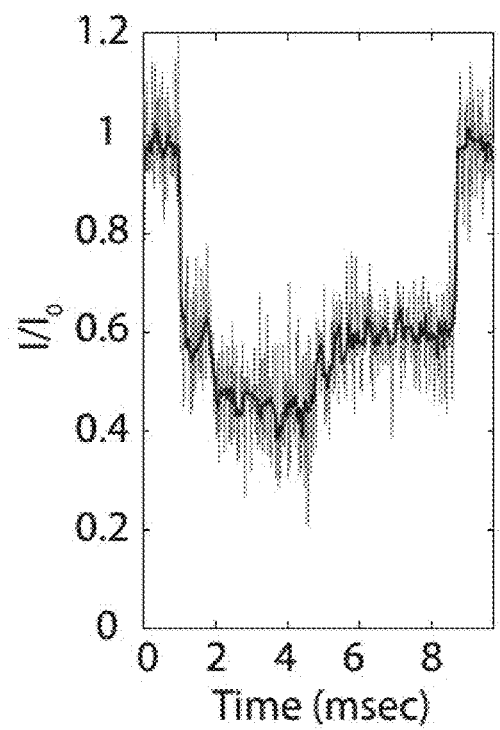
Figure 7C:
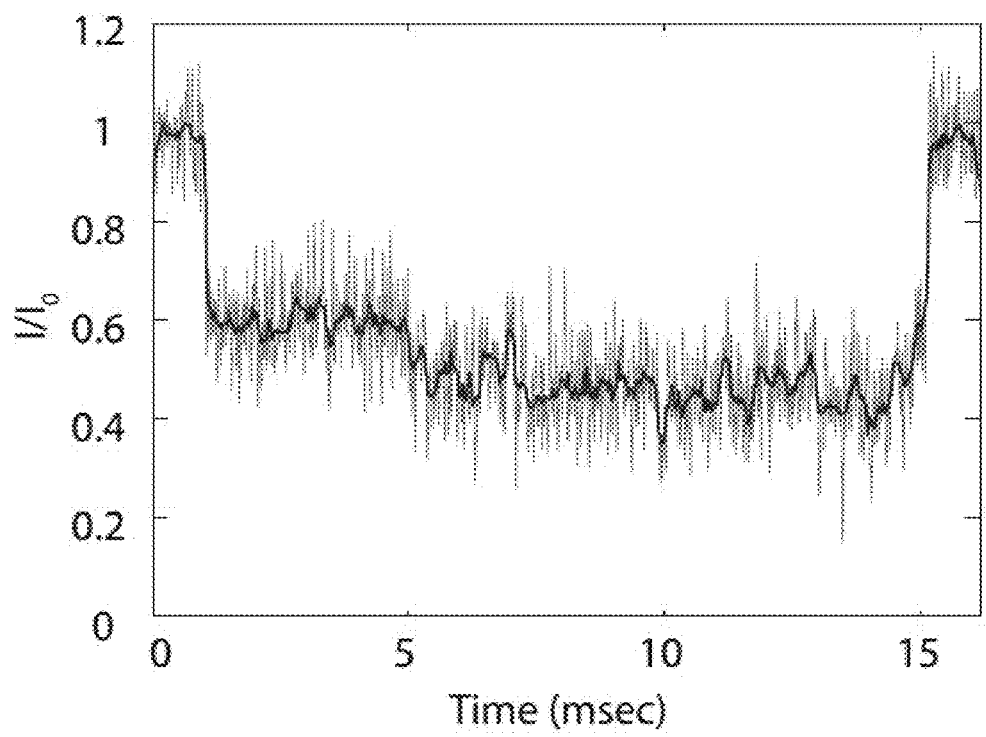
Figure 7D:
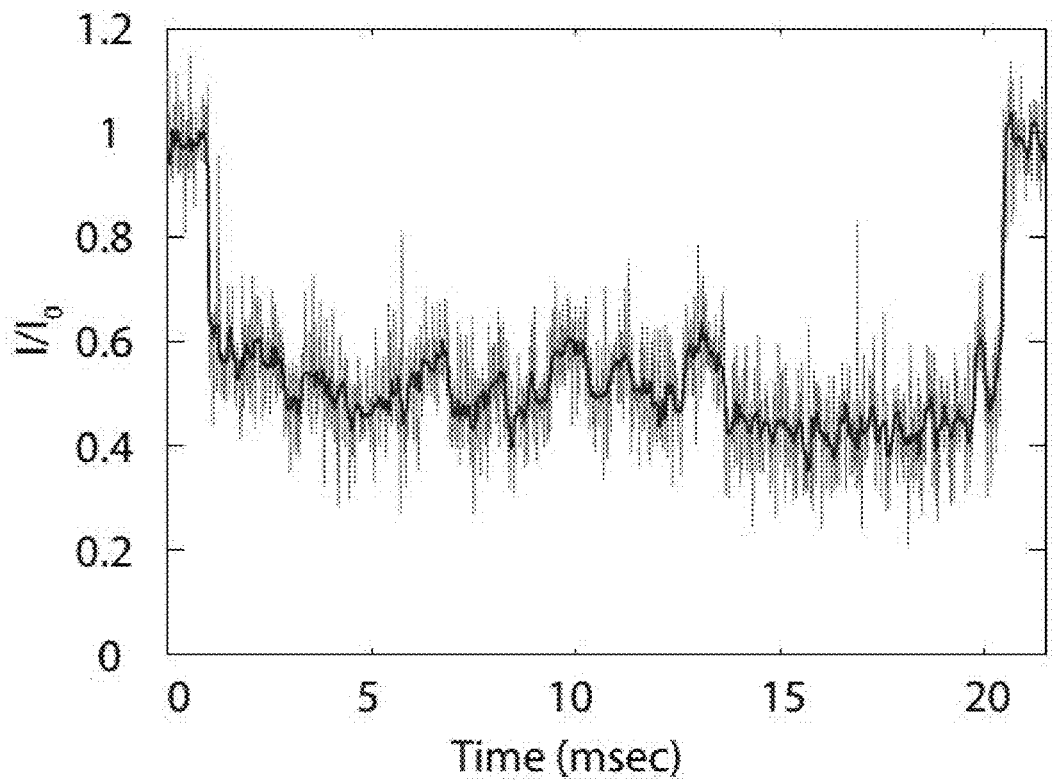
Figure 7E:
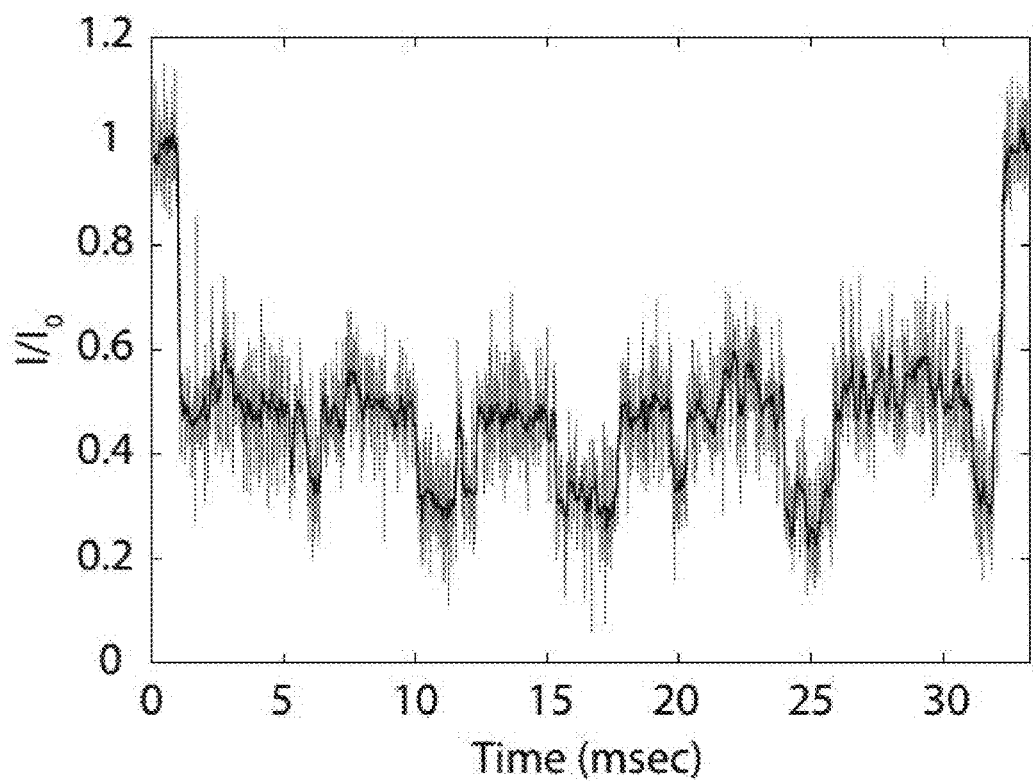

FIGS. 6A-6B are discussed with respect to a nanopore sensor system as described above with respect to FIGS. 2A-2B. Notably, the nanopore sensor system should include at least one nanopore and at least one protein shuttle. FIG. 6A shows an exemplary methodology 600A for characterizing shuttle capture in a nanopore sensor.

The methodology 600A can begin at step 610 by collecting time-dependent current blockage signatures for a plurality of different bias voltages at a nanopore sensor. Each single protein capture, whether transient or permanent, produces its own unique, time-dependent current blockage signature that can be uniquely identified. The time-dependent current blockage signature can comprise a measurement of nanopore current as a function of time during a shuttle capture event. Example time-dependent current blockage signatures for transient and permanent events are shown in FIGS. 7A-8B.

Figure 8A:
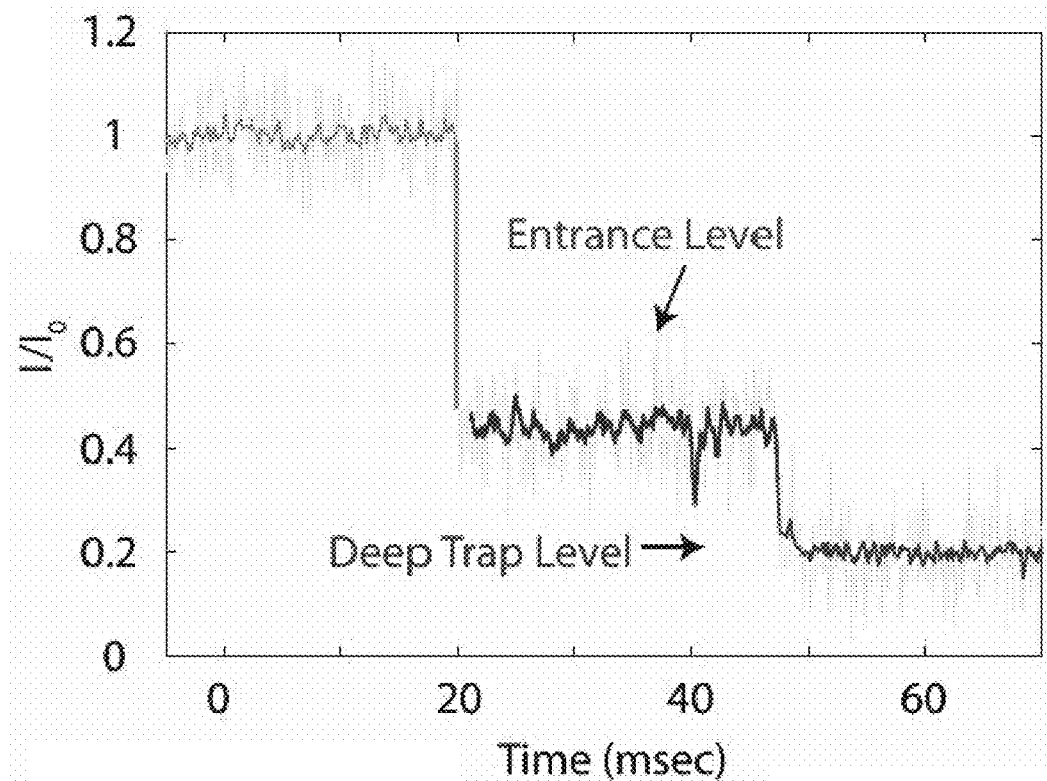
FIGS. 8A-8B show exemplary time-dependent current blockage signatures for permanent events, according to an embodiment of the present disclosure.
Figure 8B:
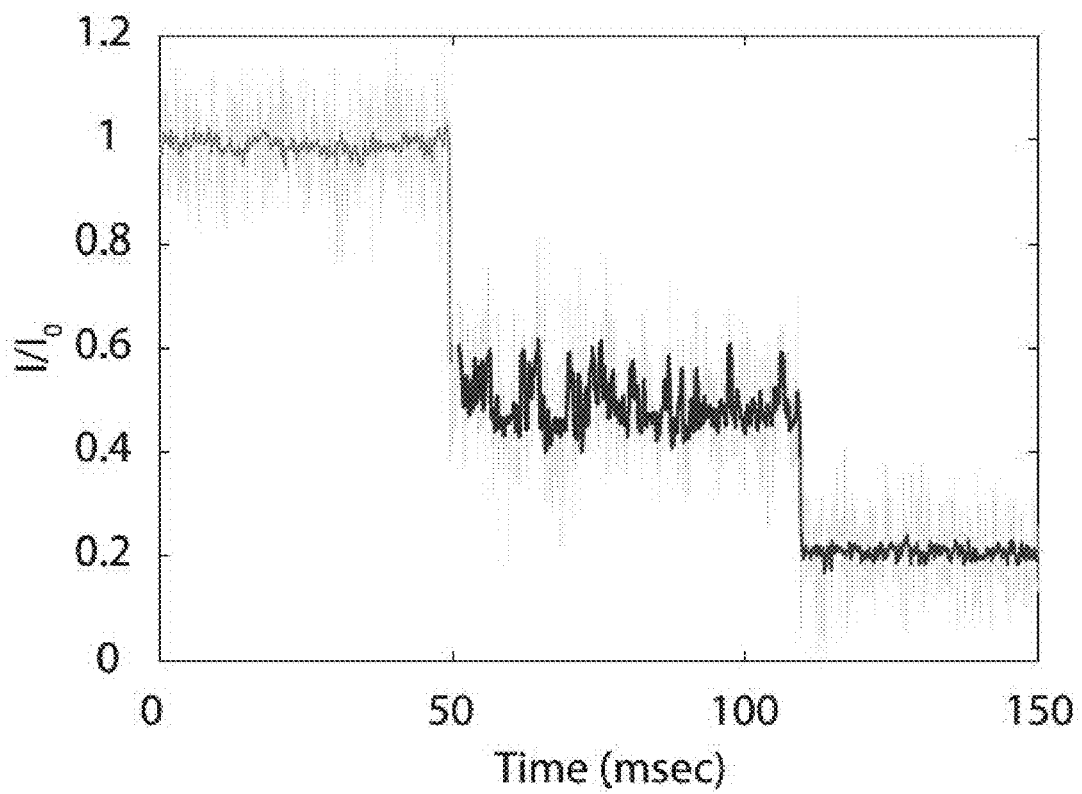

Referring back to FIG. 6A, the method can then proceed to step 612 and classify the time-dependent current blockage signatures into permanent events and transient events. Permanent events can be identified for any one of the plurality of time-dependent current blockage signatures failing to show a return to an initial current level (as shown in FIGS. 8A-8B). Transient events can be identified for any one of the plurality of time-dependent current blockage signatures which shows a return to an initial current level (as shown in FIGS. 7A-7E).

The method can then provide for generating a protein dynamics landscape (PDL) for the transient event signatures at step 614. These PDLs can be generated for each of the plurality of bias voltages. The PDLs comprises a collection of blockage spectra. Each of the collection of blockage spectra can comprise a histogram of blockage values for a selected duration. In some examples, the blockage spectra can comprise an average of nanopore current data sampled at a fixed interval to yield histogram data points. A length of the fixed interval can be at least as long as a sampling period of the nanopore current data. For example, the length of the fixed interval can be 160 microseconds. The nanopore current data can comprise a ratio of a change in the current from an input current to the input current.

In some examples, the selected duration of the particular blockage spectra can be between 0 seconds and 2 microseconds, between 0 seconds and 5 microseconds, between 0 seconds and 10 microseconds, between 0 seconds and 30 microseconds, between 0 seconds and 100 microseconds, between 0 seconds and 500 microseconds, or between 0 seconds and 1000 microseconds.

PDL plot generation is discussed further with respect to FIGS. 10A-10F.

Referring back to FIG. 6A, the method can then proceed to step 616 to identify an entrance level blockage value based on the permanent event signatures. In some examples, the identifying step can comprise generating an additional PDL for the permanent event signatures for at least one of the plurality of bias voltages. The identifying step can further comprise selecting the entrance level blockage value to correspond to a common lower peak of the blockage values for the collection of blockage spectra in the additional PDL. The entrance level blockage can be selected to correspond to a level that often precedes, within a single trapping event, and is lower than the blockage value observed when the shuttle protein is permanently trapped in the nanopore.

The method can then comprise selecting one of the plurality of bias voltages corresponding to a PDL for the transient event signatures based on the peak blockage values at step 618. The collection of blockage spectra can provide peak blockage values that are substantially equal to the entrance level blockage value.

The PDL is generated form a collection of blockage spectra. The different blockage spectra in a PDL for permanent events can be generated with inclusion of all permanent events recorded with application of a particular voltage between the fluidic chambers. For each individual blockage spectrum within a PDL, the histogram is generated from current data within only an initial time period of each event, from the event start to a maximum time. The maximum time is chosen differently for the different individual blockage spectra within a PDL, for example 2 milliseconds, 5 milliseconds, 10 milliseconds, 30 milliseconds, 100 milliseconds, 500 milliseconds, and 1000 milliseconds.

The PDL comprises a collection of blockage spectra. Each of the collection of blockage spectra can comprise a histogram of blockage values for permanent events where these blockage values are obtained for each permanent event from the start of the event and up to a maximum time after event start. The method can then comprise identifying a permanent level blockage value based on permanent event signatures. The permanent blockage level is a blockage level that, once reached, rarely ever changes unless the shuttle is ejected, for example, by reversing the polarity of the applied voltage. The method can further comprise identifying an entrance level blockage value based on permanent event signatures and the PDL plots for the permanent events. The method can then comprise selecting one of the plurality of bias voltages corresponding to a PDL for the transient event signatures. The collection of blockage spectra can reveal peaks at blockage values that are substantially equal to the permanent level blockage value and/or to the entrance level blockage value.

In some examples, selecting the entrance blockage level can further comprise fitting a first Gaussian distribution to each of the collection of blockage spectra and fitting a second Gaussian distribution to a particular blockage spectra. The second Gaussian distribution can be subtracted from the first Gaussian distribution to yield resultant distribution. The entrance level blockage value can be determined from a peak of the resultant distribution. This method is discussed further with respect to FIGS. 14A-14G.

Referring back to FIG. 6A, the method can optionally include an additional step of calculating a ratio of a number of permanent shuttle capture events to a number of transient shuttle capture events for each of the plurality of bias voltages. Based on the calculated ratios, the method can then comprise determining a threshold bias voltage to achieve a preferred ratio.

FIG. 6B shows an exemplary methodology 600B for determining blockage levels of at least one nanopore in the nanopore sensor. The method can provide for first collecting a plurality of time-dependent current blockage signatures for a selected bias voltage in step 620.

The method can then provide for calculating a duration of a shuttle capture event and a blockage percentage for the shuttle capture event in step 622. Calculating the duration of the shuttle capture event and the blockage percentage can be based on the collected plurality of time-dependent current blockage signatures. For example, a change in the nanopore current while a protein molecule is attached relative to the nanopore current while no protein molecule is attached can identify what percentage of the original nanopore current is blocked by the shuttle capture event. A duration can be identified from a length of time of the shuttle capture event.

The method can then comprise determining a blockage level based on a distribution characteristic of the plurality of time-dependent current blockage signatures at step 624. In some examples, step 624 can comprise determining whether the duration of the shuttle capture event falls in a range between a pre-defined minimum duration and a pre-defined maximum duration.

For example, a range of 0 milliseconds to 2 milliseconds corresponds to a blockage peak at 40% current blockage; a range of 0 milliseconds to 5 milliseconds corresponds to blockage peaks at 45% and 52% current blockage; a range of 0 milliseconds to 10 milliseconds corresponds to blockage peaks at 40%, 45%, and 52% current blockage; a range of 0 milliseconds to 30 milliseconds corresponds to a blockage peak at 57% current blockage; a range of 0 milliseconds to 100 milliseconds corresponds to blockage peaks at 40%, 45%, 52%, and 57% current blockage; a range of 0 milliseconds to 500 milliseconds corresponds to blockage peaks at 40%, 45%, 52%, and 57% current blockage; and a range of 0 milliseconds to 1000 milliseconds corresponds to a blockage peak at 80% current blockage.

Blockage levels, as identified in the PDLs, are different when just a protein molecule is trapped by the pore from when a target molecule is attached to the protein shuttle and linked to the pore. The difference in the blockage levels can identify that a target molecule is linked. For example, when Avidin is trapped alone in ClyA, the PDL peaks are at blockage levels of 40%, 45%, 52%, and 57%, although these peaks will change when a target molecule is attached to Avidin.

In some examples of step 624, the determining step can comprise identifying a particular blockage event as transient if the length of time of the particular blockage event is less than a threshold period of time. The threshold period of time can be any period of time less than 1 second.

Therefore, FIG. 6B shows how variety of abilities according to an embodiment of method 600B. For example, the different individual spectra within a PDL for permanent events can be identified by a length of time since a start of the events. The PDLs for transient events, and the comparison of PDLs for transient and permanent events, can identify various trap states of a molecule or of a protein shuttle. The PDLs can also identify an orientation of the molecule relative to the nanopore. For example, the methods of the present application identify that Avidin has a particular orientation relative to the ClyA nanopore when Avidin is in the state AC80. The PDLs for permanent events are particularly relevant for analyzing a target molecule linked to a protein shuttle. When a target molecule is linked to the protein shuttle, the permanent event PDLs will have new blockage level values and new heights of the corresponding peaks in the individual spectra of a PDL. The heights of these peaks change from spectrum to spectrum within a PDL to reveal the global dynamics of the linked target molecule. The heights changes from spectrum to spectrum is a result of the linked target molecule because the shuttle molecule is captured stably in a permanent state.

As discussed later with regards to FIGS. 14A-14G, the peak heights can be obtained by fitting the individual spectra with sums of Gaussian distributions.

In some examples, the method 600B can identify an expected protein molecule orientation based on the blockage level. This is discussed further with respect to FIGS. 11A-11E.

FIGS. 7A-8B show a collection of single molecule capture events in the 1.66 nS ClyA nanopore. FIGS. 7A-8B show X-Y plots of the observed current, I(t), during each capture event, divided by the measured open-nanopore current, $I_0$. $I_0$ is also referred to as the input current for the purposes of the present disclosure. The plotted events in FIGS. 7A-7E show the time-dependent blockage for transient events of increasing duration. Most transient events are simple, having only a single blockade level as in the first event in FIG. 7A. The longer transient events, though not the most common, demonstrate that sometimes transitions between levels are observed. In a first-pass step of analysis, each of these Transient Captures can be characterized by two numbers, namely, the duration of the event, and the average "blockage" during the event. The "blockage" is defined to be $(I_0 - I(t))/I_0$, averaged over each blockage event's duration.

FIGS. 8A-8B show the current traces for two Permanent Captures. Each of these events has an interesting time structure. As with most Permanent Capture events, they start with a preliminary, fluctuating blockage that is followed by a deep and quiet permanent blockage. Permanent Captures are characterized by the time duration and average blockage during the preliminary part of the event.

In some instances, an entrance level of a protein molecule can be identified for a particular protein molecule-nanopore combination. For example, Avidin has an entrance level when interacting with the ClyA nanopore. Therefore, Avidin has a particular orientation that it must enter the nanopore in order to subsequently enter into a permanently trapped state.

Figure 13:
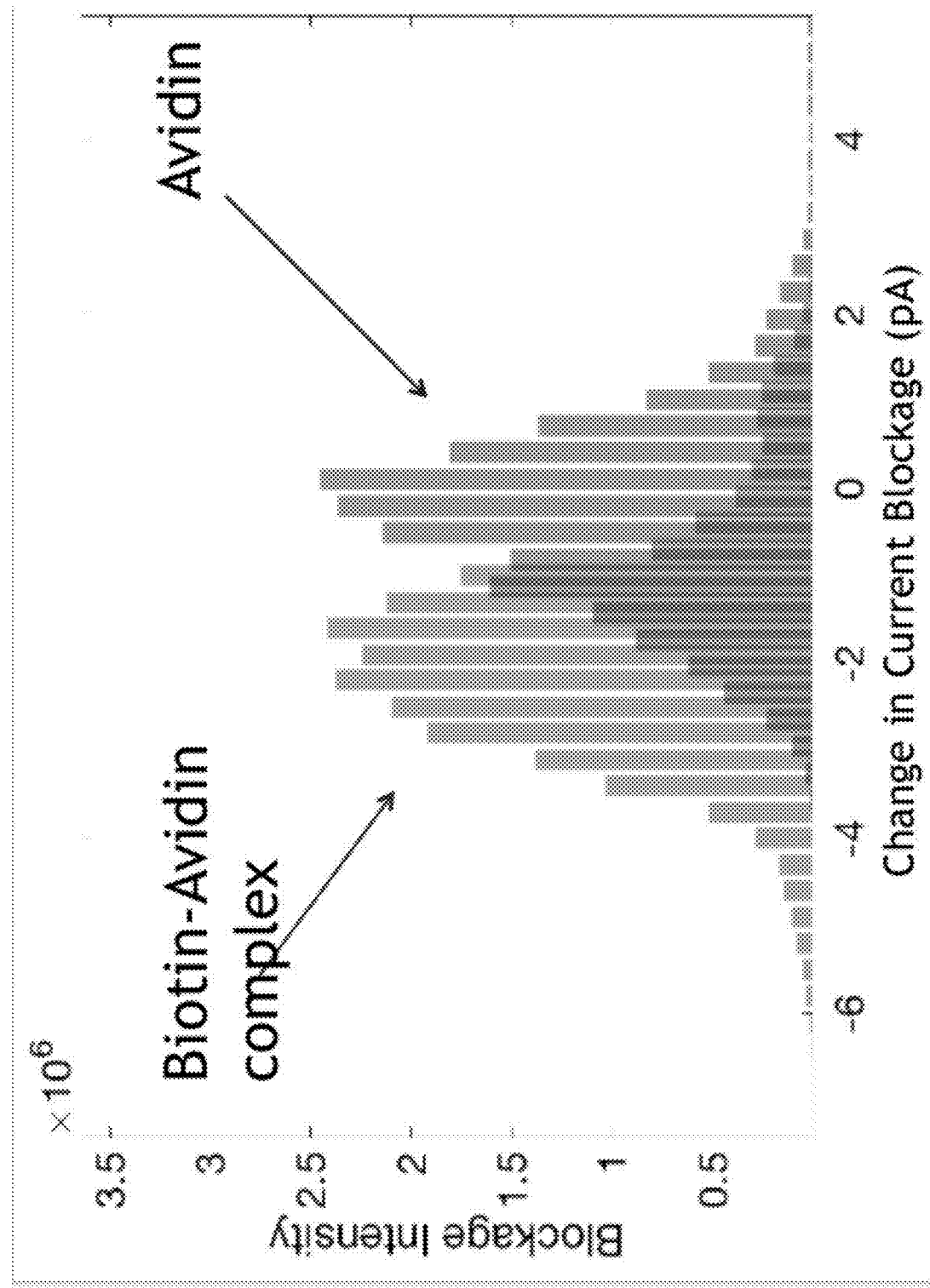
FIG. 13 shows a comparison of change in current blockage for Avidin versus an Avidin biotin complex, according to an exemplary embodiment of the present disclosure.
Figure 14A:
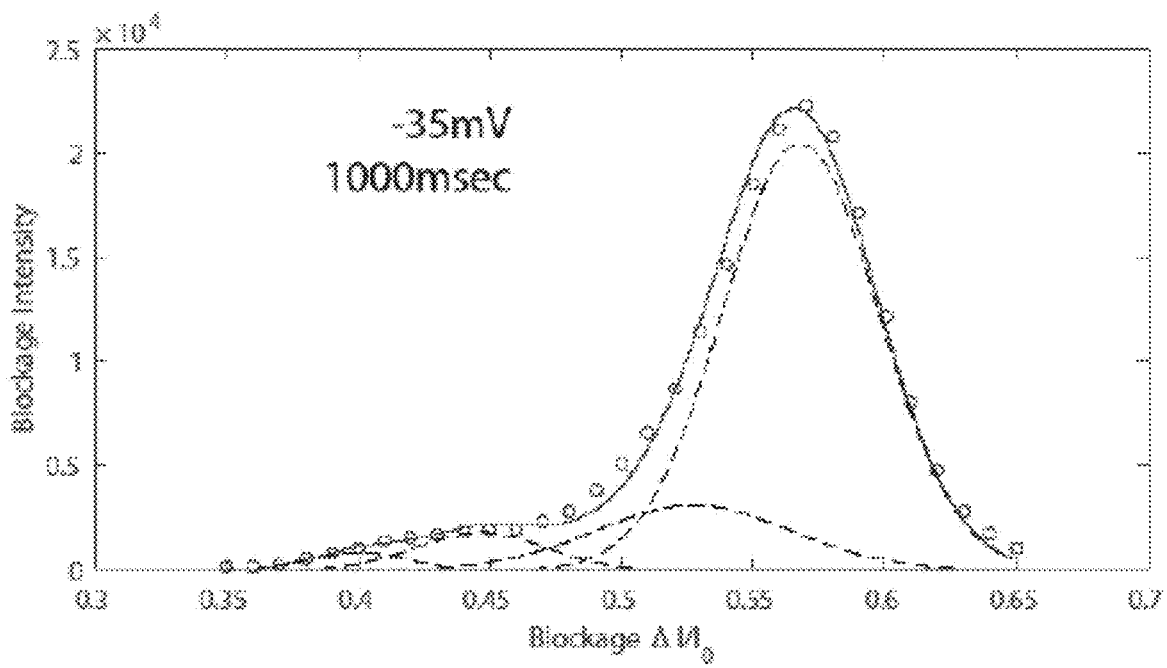
FIGS. 14A-14G show exemplary Gaussian fits to the PDL histogram plots, according to an embodiment of the present disclosure.
Figure 14B:
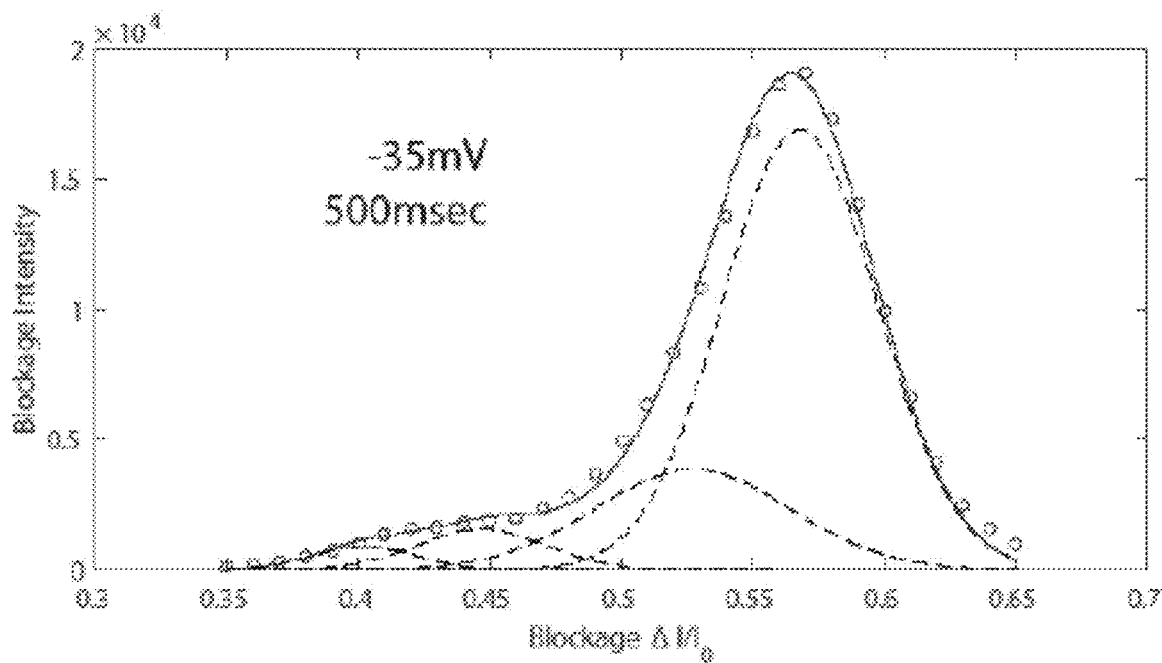
Figure 14C:
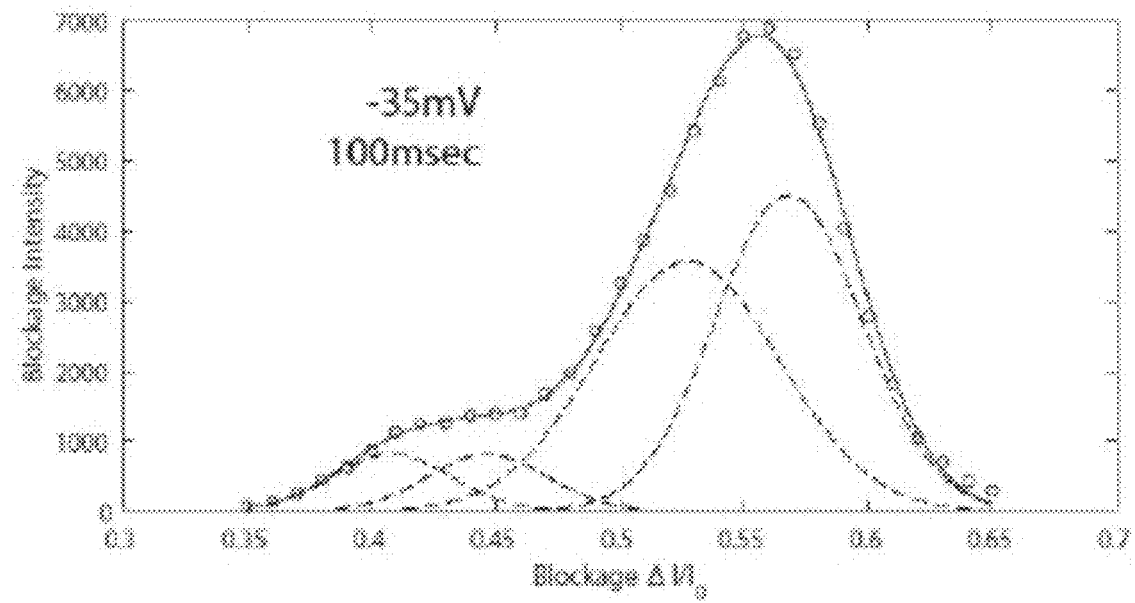
Figure 14D:
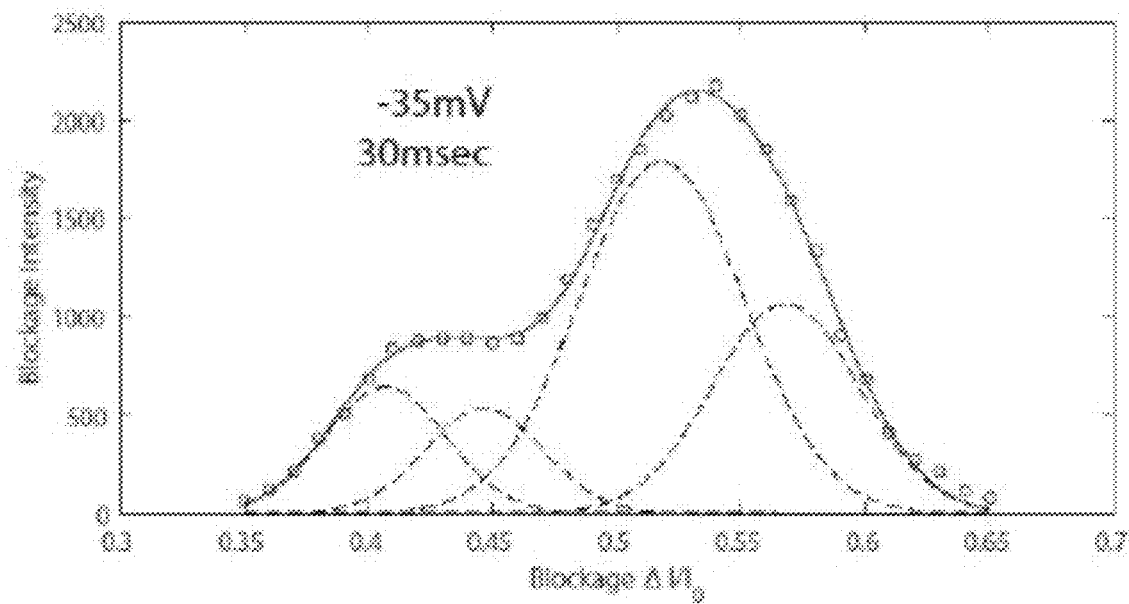
Figure 14E:
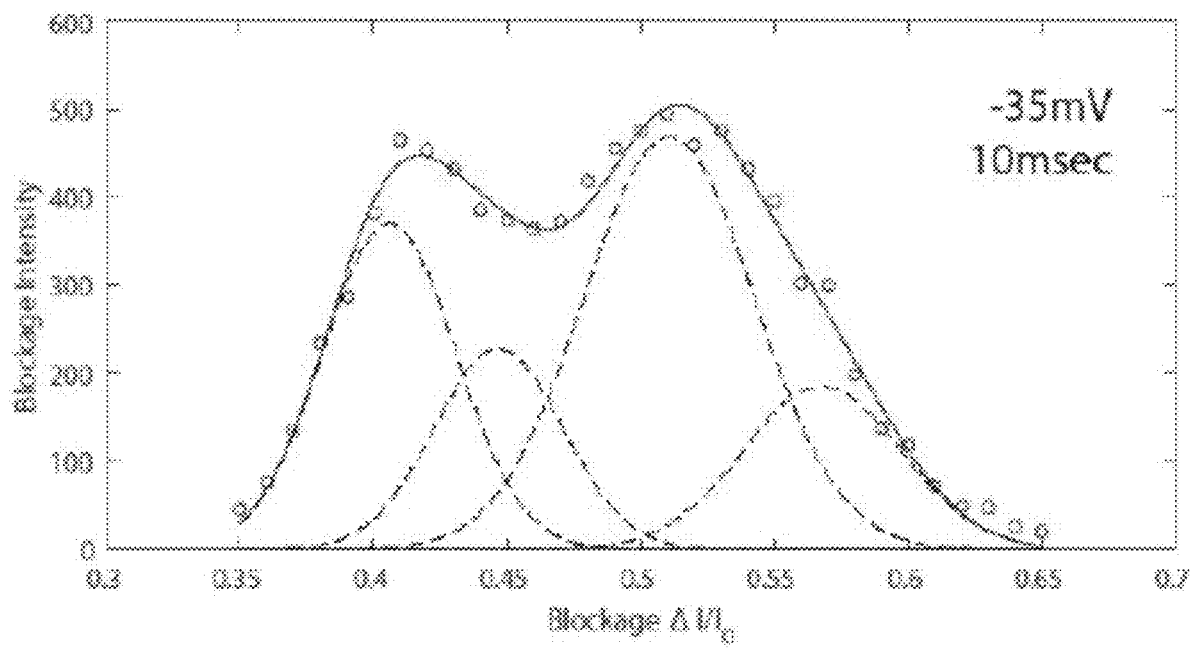
Figure 14F:
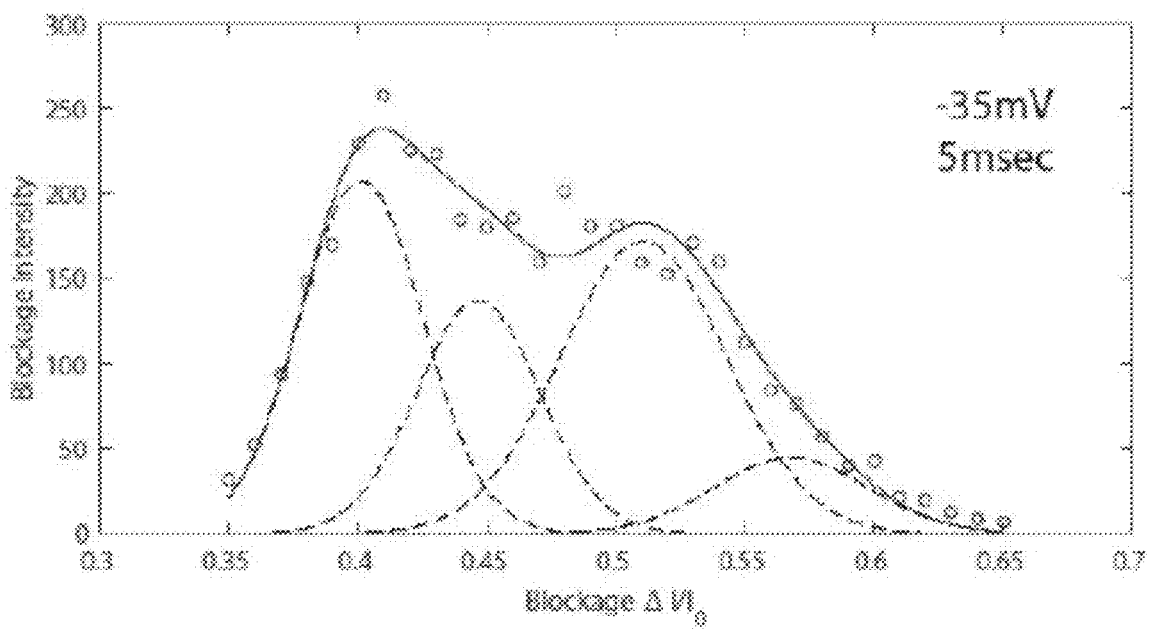
Figure 14G:
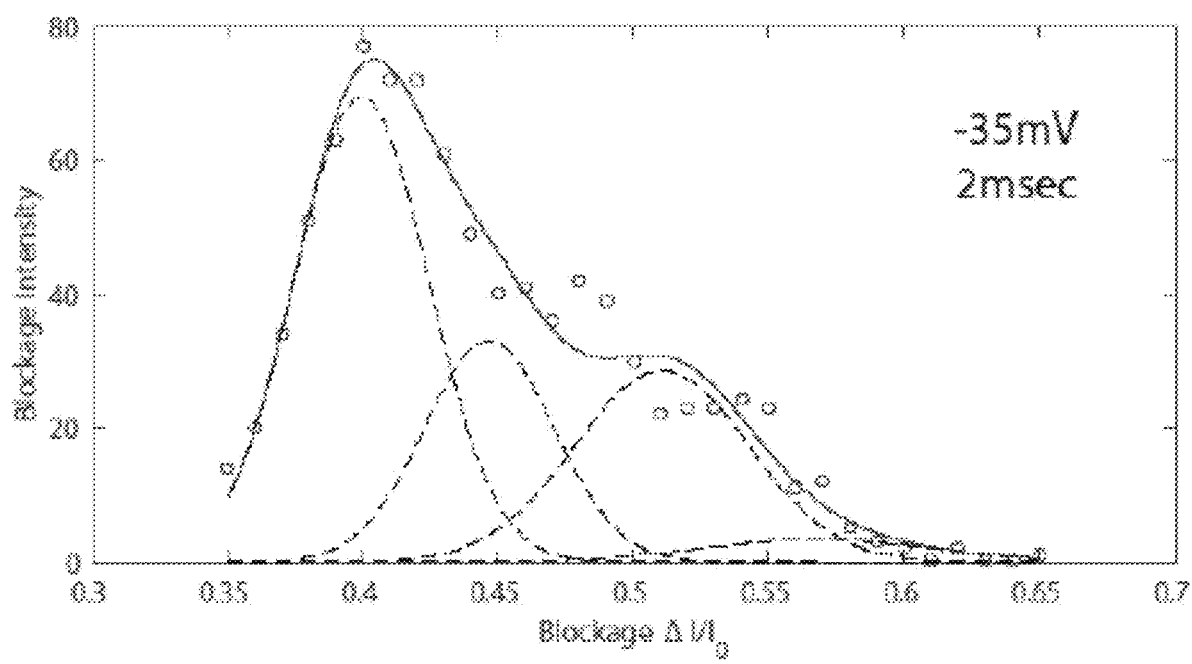

The fact that a permanently trapped state with well-defined orientation exists is important for the shuttle platform. The state can be used to transport other molecules to the pore, where they can be stably held in a particular orientation for analysis. The PDL method can then be used to reveal the dynamics of the analyte/target molecule thus transported to the pore. In this situation with Avidin trapped in the pore (i.e., the shuttle docket in the pore a stable current background is provided (which is the low-noise residual current in the stably trapped state of Avidin). Perturbations of this current level can then be interpreted as being due to the analyte molecule and its dynamics which is the molecule and dynamics of interest here. PDL plots could now be generated based on the time-dependent current or blockage signal of an event where the interesting current or blockage is the current or blockage difference relative to that of the permanent level of just Avidin in the pore. This is discussed further with respect to FIG. 13.

FIGS. 9A-9D show scatter plots of these parameters for each Transient Capture event (light points) reflecting this characterization. Each light point belongs to one protein capture. As shown in FIGS. 9A-9D, as the Transient Capture event duration increases from a few hundred microseconds to a few hundred milliseconds, the average blockage slowly increases. This results from the existence of multiple discrete blockage levels that are averaged over each event in the scatter plot.

Permanent Capture event are shown in the scatter plots of FIGS. 9A-9D as the darker points. FIGS. 9A-9D suggest that the average blockage is clearly independent of duration and is close to that of the longest transient events. This suggests that prior to capture to a deep permanent blockage level, the protein often passes through an intermediate state of variable duration.

Figure 9A:
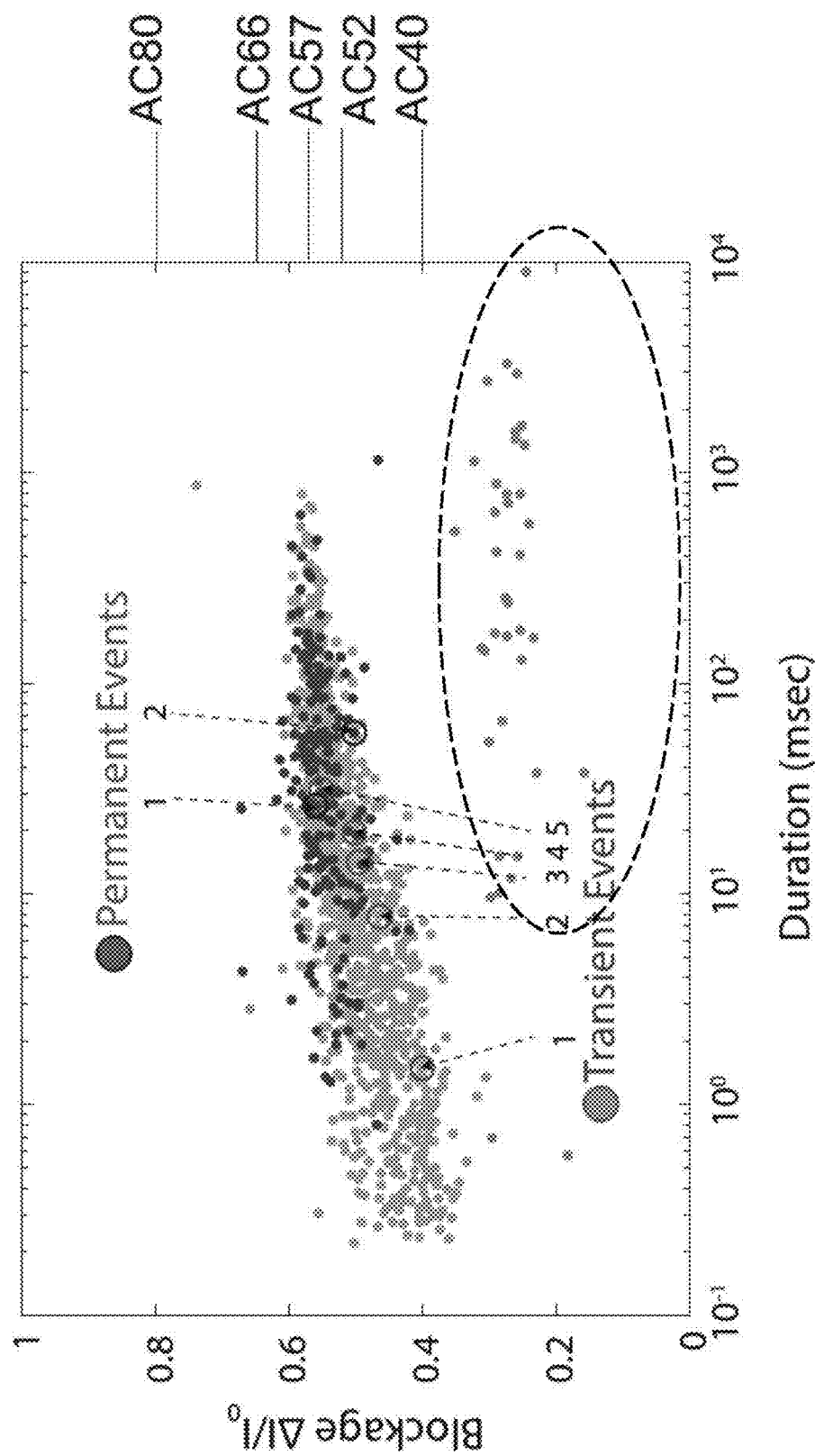
FIGS. 9A-9D show a comparison of exemplary nanopore current data as compared between transient and permanent events, according to an embodiment of the present disclosure.
Figure 9B:
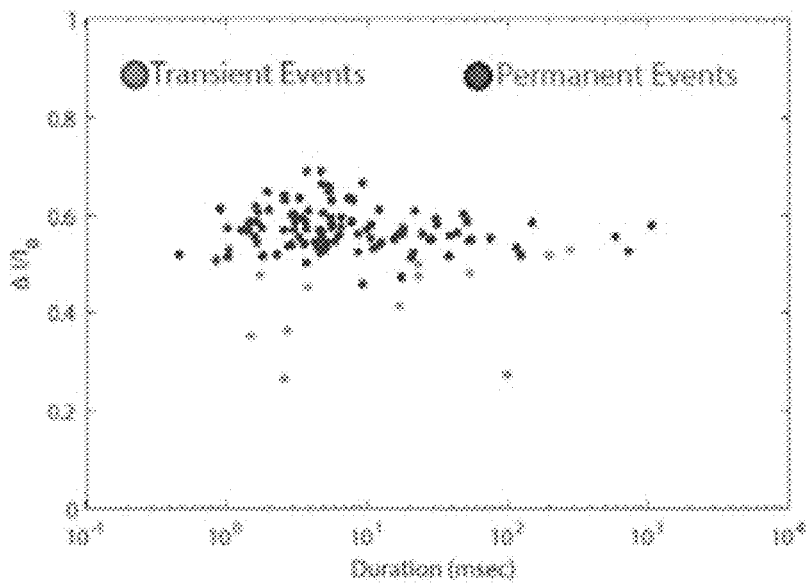
Figure 9C:
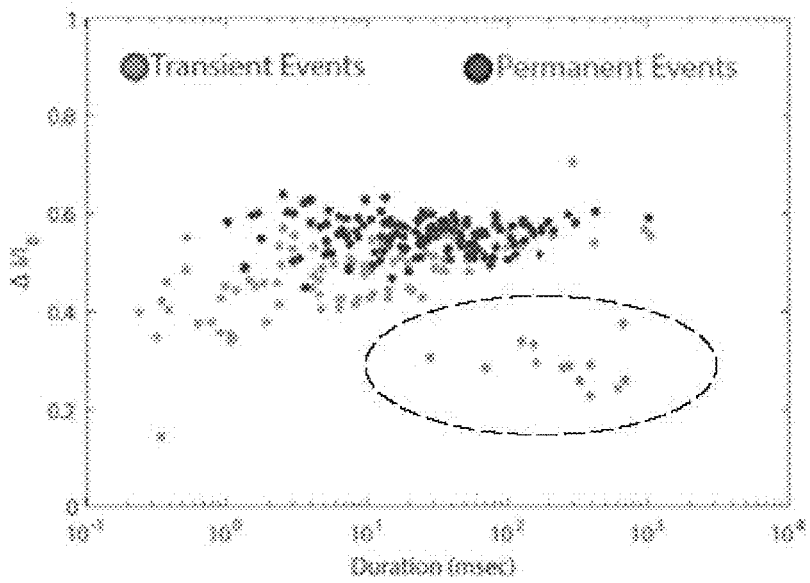
Figure 9D:
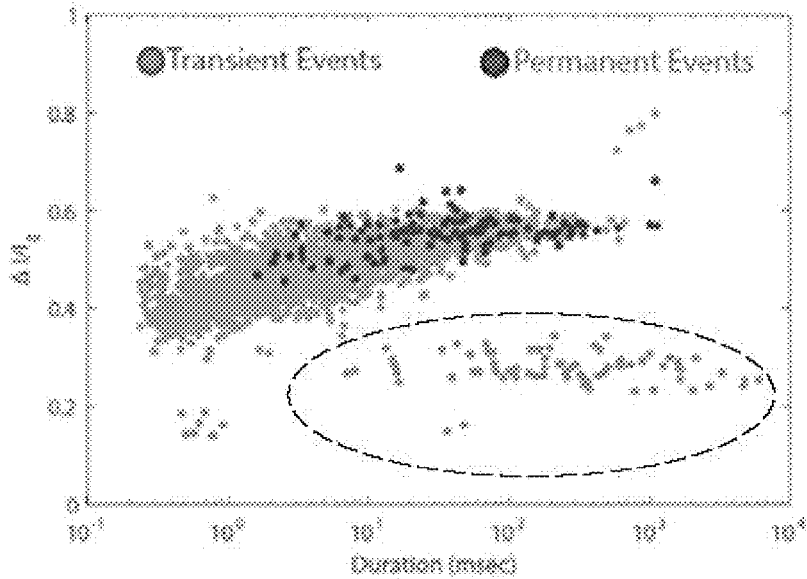

The circled regions in FIGS. 9A, 9C, and 9D show the noisy nature of the data collection. These events have a blockage level of 20-30% which is lower than would be expected if a protein shuttle bonded to the nanopore. Therefore, the data points in the circled region most likely reflect molecular fluctuations in the structure of the nanopore. In some of these instances, the nanopore system can be reset so that the nanopore returns to its original configuration with a proper input current. These data points are excluded from data analysis.

Figure 10A:
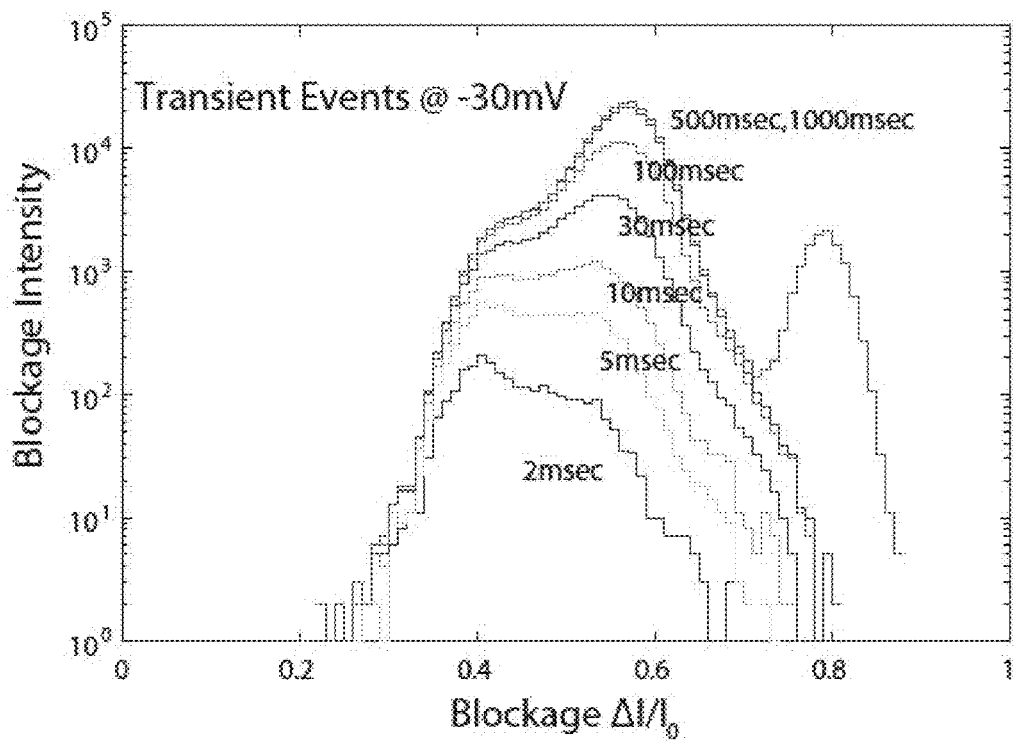
FIGS. 10A-10F show exemplary PDL histogram plots, according to an embodiment of the present disclosure.
Figure 10B:
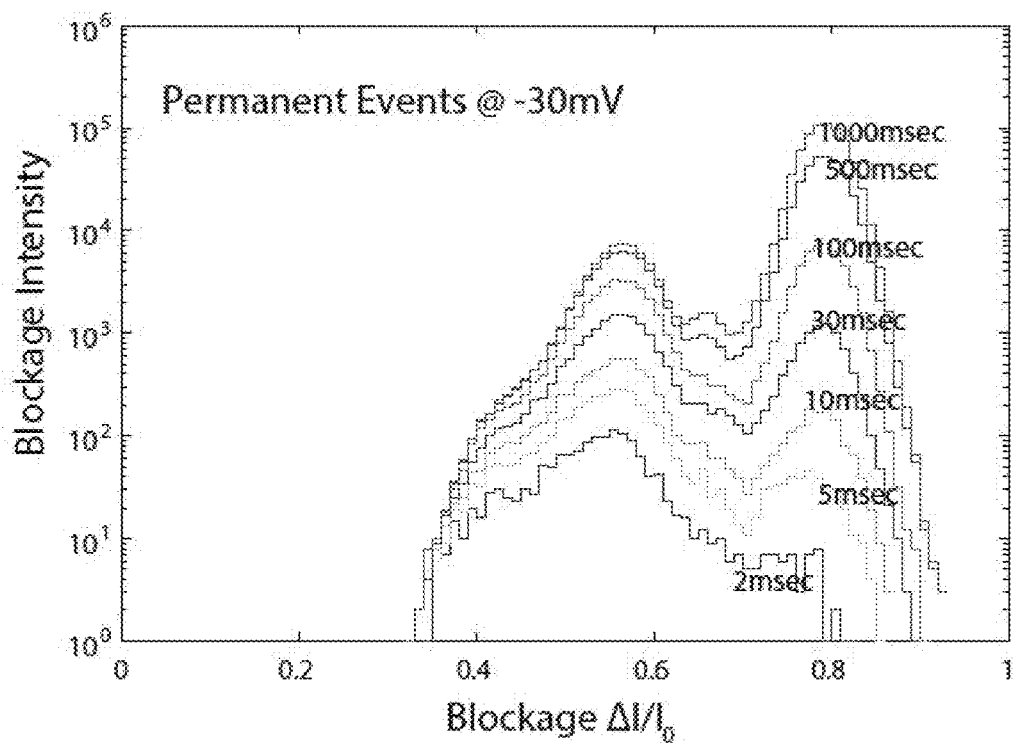
Figure 10C:
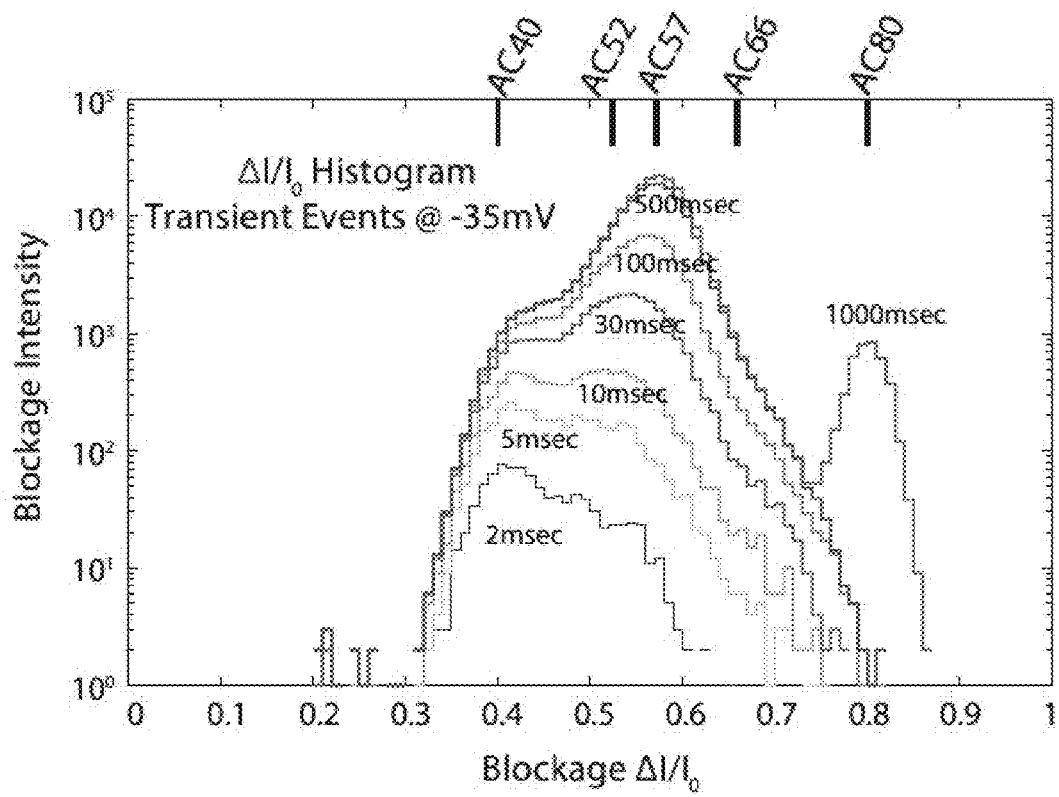
Figure 10D:
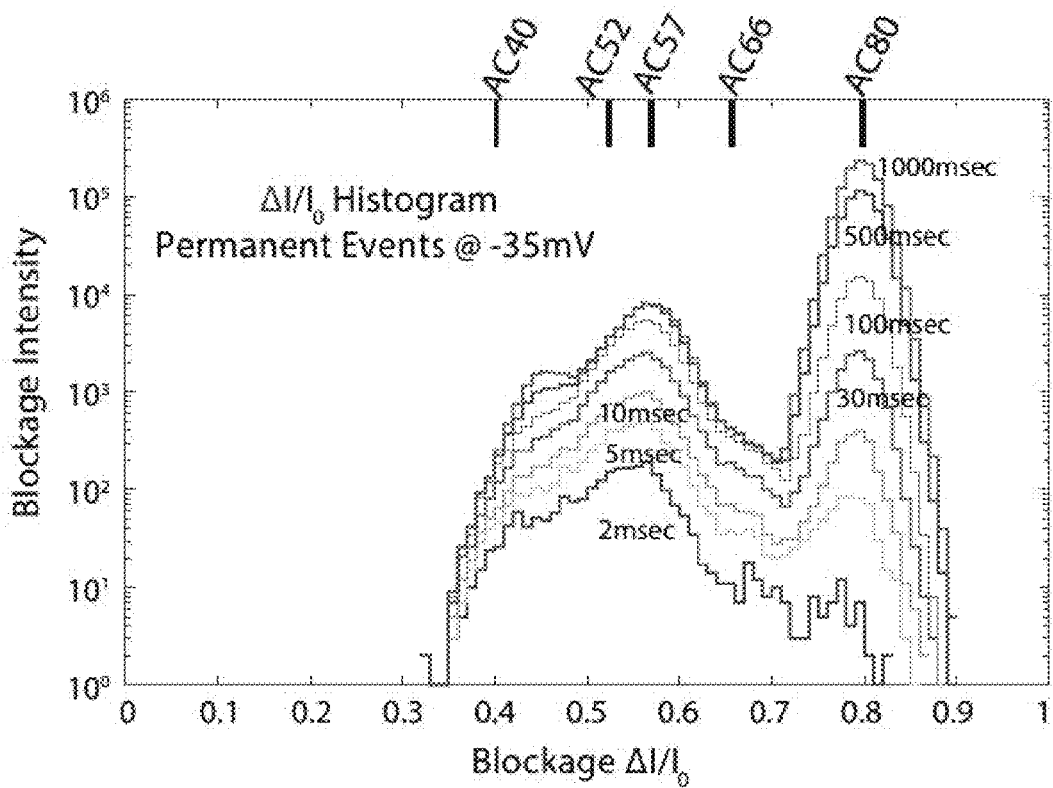
Figure 10E:
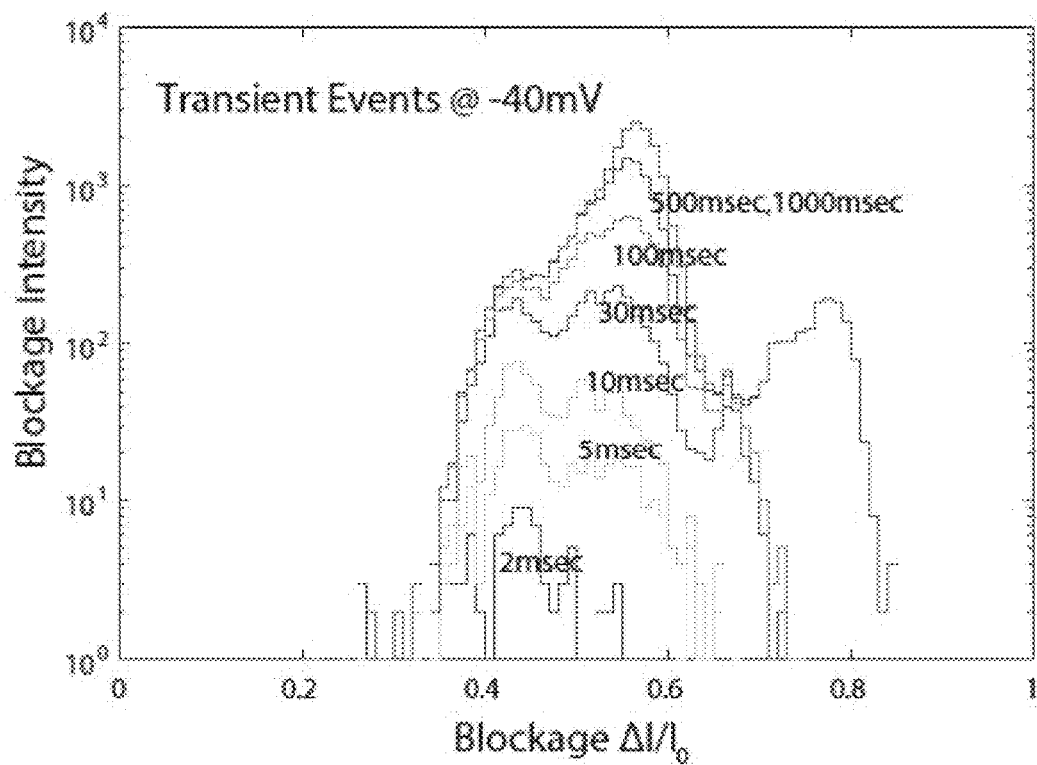

FIGS. 10A-10F show exemplary PDL histogram plots, according to an embodiment of the present disclosure. The existence of discrete blockage levels and their time-dependent populations are shown dramatically and quantitatively in the Protein Dynamics Landscape (PDL) plots in FIGS. 10A-10F. These plots can be generated according to the methodology discussed with respect to FIG. 6A. In FIGS. 10A, 10C, and 10E, only transient events that last for times less than a specified $\tau_{trans}$ are plotted. The amount of time spent (in units of 160 microseconds) at each blockage level for all these events is determined and a histogram of the time spent at each level is generated. This histogram can be referred to as a blockage spectrum. A collection of such blockage spectra, for a set of increasing $\tau_{trans}$ values, can then be termed a Protein Dynamics Landscape (PDL). For example, $\tau_{trans}$ can be 1 second.

Figure 10F:
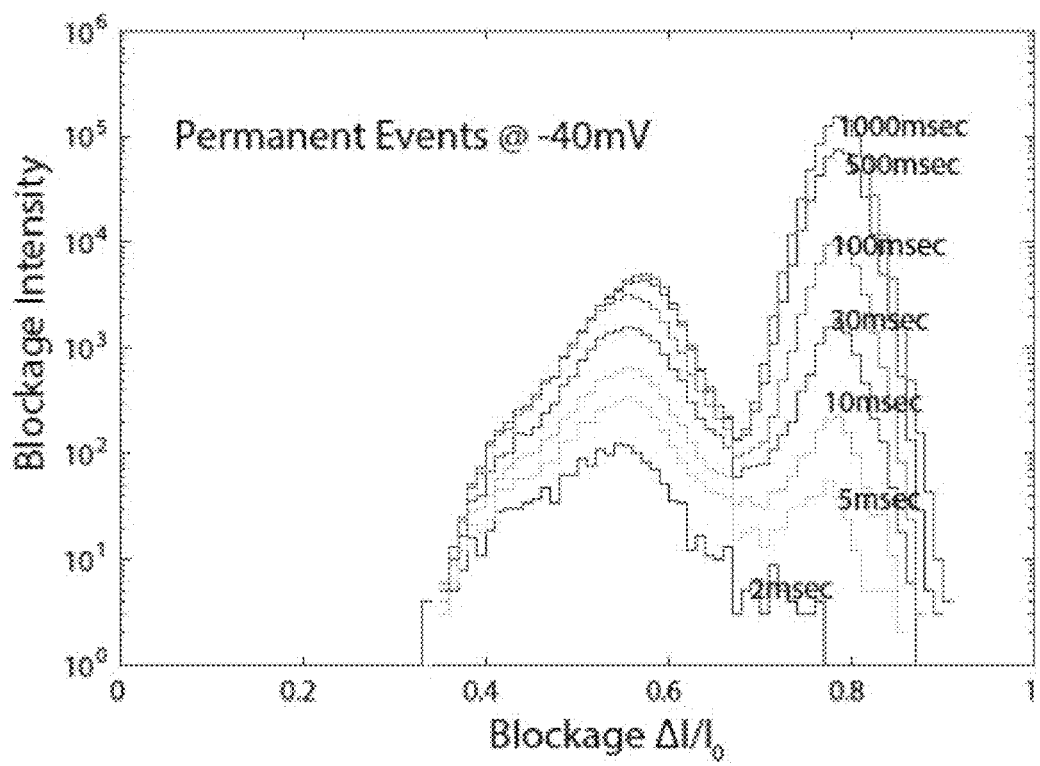

The PDLs for FIGS. 10A-10B are obtained for a fixed bias voltage of −30 mV, FIGS. 10C-10D have a fixed bias voltage of −35 mV, and FIGS. 10E-10F have a fixed bias voltage of −40 mV. The PDL plots reveal several peaks, corresponding to discrete blockage levels for Avidin in ClyA. Note that deeper blockage levels last longer than shallower levels.

Permanent capture event data are provided in FIGS. 10B, 10D, and 10F. In these graphs, all permanent capture events are considered together and each histogram refers to the accumulated time (in units of 160 microseconds) a blockage value appears up until $\tau_{perm}$ capture events start (which is when Avidin first enters the nanopore). The deepest blockage level is revealed to be maximally populated for the longest times.

FIG. 10C shows a single peak centered at 40% blockage (Avidin Capture) AC40 for events lasting for 2 ms or less. FIGS. 10A and 10E provide plots like this for −40 mV and −30 mV. As longer events are included (i.e., as $\tau_{trans}$ is increased), a second peak emerges. With careful fitting, this second peak is centered at 52% blockage and denotes the level AC52. At 10 ms, the two peaks have equal intensity, and at 30 ms, the AC52 peak dominates. For longer times, a larger and separate (AC57) peak at 57% blockage dominates. FIG. 10A shows a few very deep captures for transient events that last longer than ½ second. Here the blockage level at 80% dominates (AC80). Gaussian fits to the spectra clearly reveal a fifth peak at 45% blockage (AC45), and the fits are shown further in FIGS. 13B-13C.

The dynamic behavior of the transient event PDL plots can be compared to the permanent event PDL plots of FIGS. 10B, 10D, and 10F. During the first 2 ms of the permanent events, the spectrum is dominated by one peak: AC57. The AC40 peak is barely visible, and AC52 is missing. The spectra are generally dominated by AC57 during the early times of the permanent events, but later (>=100 ms) the AC80 peak dominates.

Table 2, below, shows the number of transient events for each blockage spectrum of FIG. 10A. Total number of permanent events at −30 mV is 131.

TABLE 2

Total Number of Transient Events at −30 mV.

| $\tau_{trans}$ | 2 ms | 5 ms | 10 ms | 30 ms | 100 ms | 500 ms | 1000 ms |
|---|---|---|---|---|---|---|---|
| Number of transient events | 566 | 943 | 1205 | 1552 | 1781 | 1854 | 1861 |

Table 3, below, shows the number of transient events for each blockage spectrum of FIG. 10E. Total number of permanent events at −40 mV is 139.

TABLE 3

Total Number of Transient Events at −40 mV.

| $\tau_{trans}$ | 2 ms | 5 ms | 10 ms | 30 ms | 100 ms | 500 ms | 1000 ms |
|---|---|---|---|---|---|---|---|
| Number of transient events | 20 | 35 | 48 | 73 | 88 | 93 | 94 |

Figure 11A:
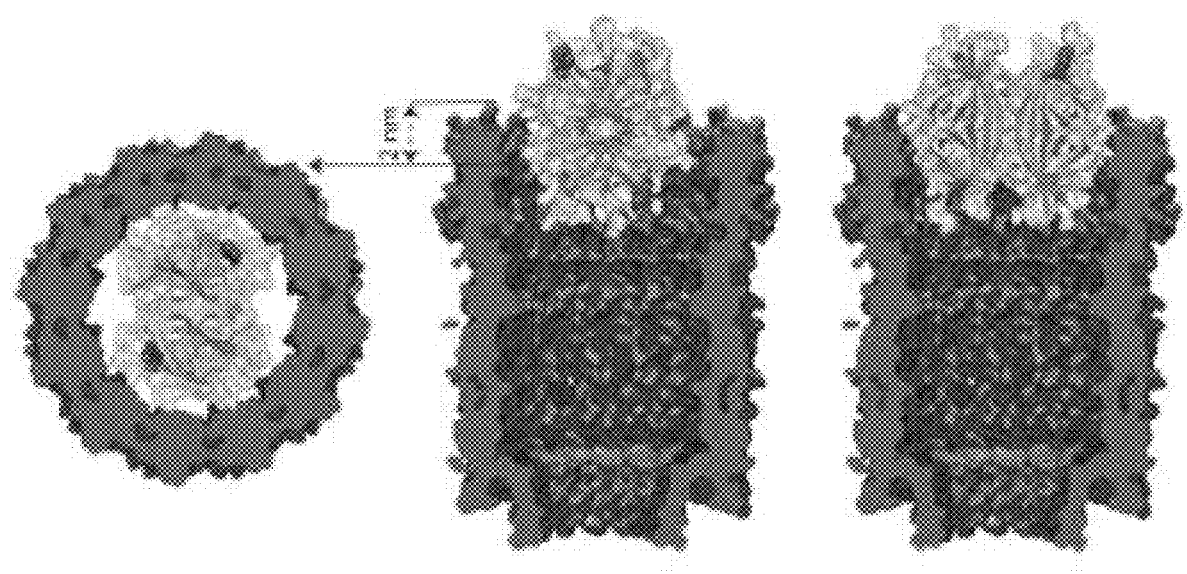
FIGS. 11A-11E demonstrate various exemplary protein molecule orientations, according to various embodiments of the present disclosure.
Figure 11B:
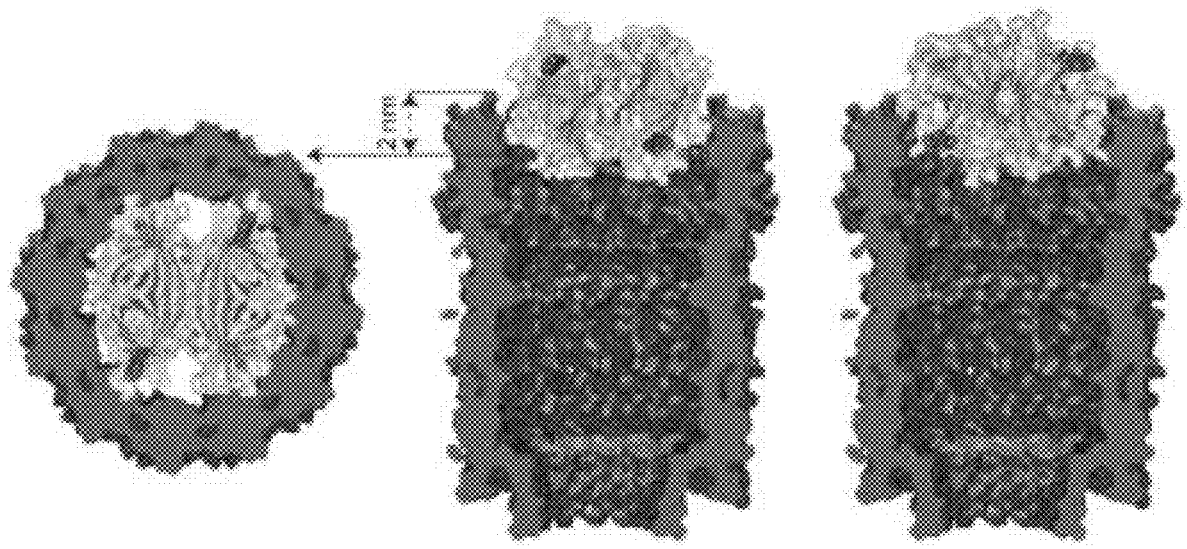
Figure 11C:
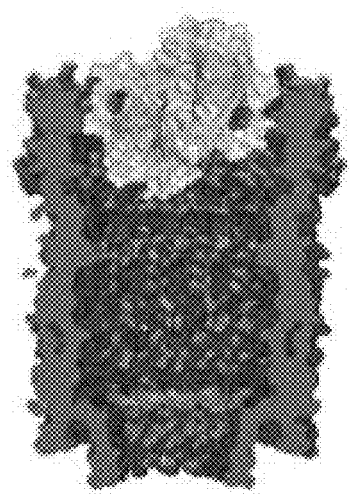
Figure 11D:
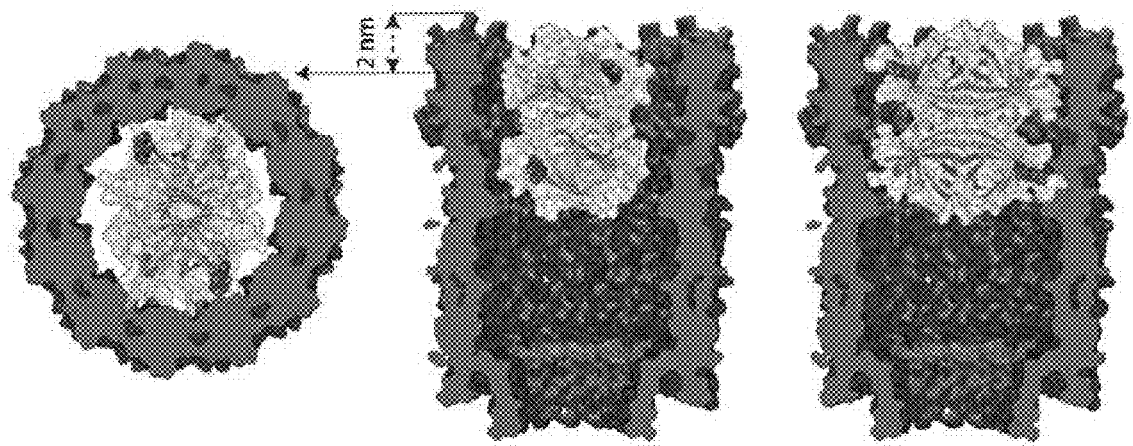
Figure 11E:
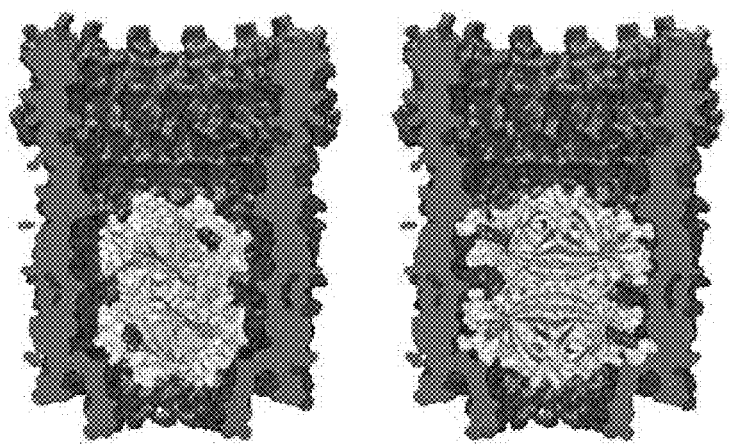

Therefore, FIGS. 10A-10F show how the PDL plots can reveal indications of the protein behavior. FIGS. 11A-11B show the expected Avidin orientation that corresponds to the AC40 states. FIG. 11C shows the expected Avidin orientation that corresponds to the AC52 state. FIG. 11D shows the expected Avidin orientation that corresponds to the AC57 state, and FIG. 11E shows the expected Avidin orientation that corresponds to the AC80 state. Therefore, FIGS. 10A-10F indicate that for the permanent trapping events, Avidin is captured into state AC57 shown in FIG. 11D, where it stays for an average of 60 ms (at −35 mV). This is followed by capture into a deeply and permanently trapped state, AC80, shown in FIG. 11E. This scenario is supported by the experimental time traces for the Permanent Capture events shown in FIGS. 8A-8B. The present methodology can also observe two weak, additional peaks in the PDLs at other bias voltages which correspond to rarely encountered, discrete levels at 66%, at AC66, and 90% blockage, respectively.

Figure 12:
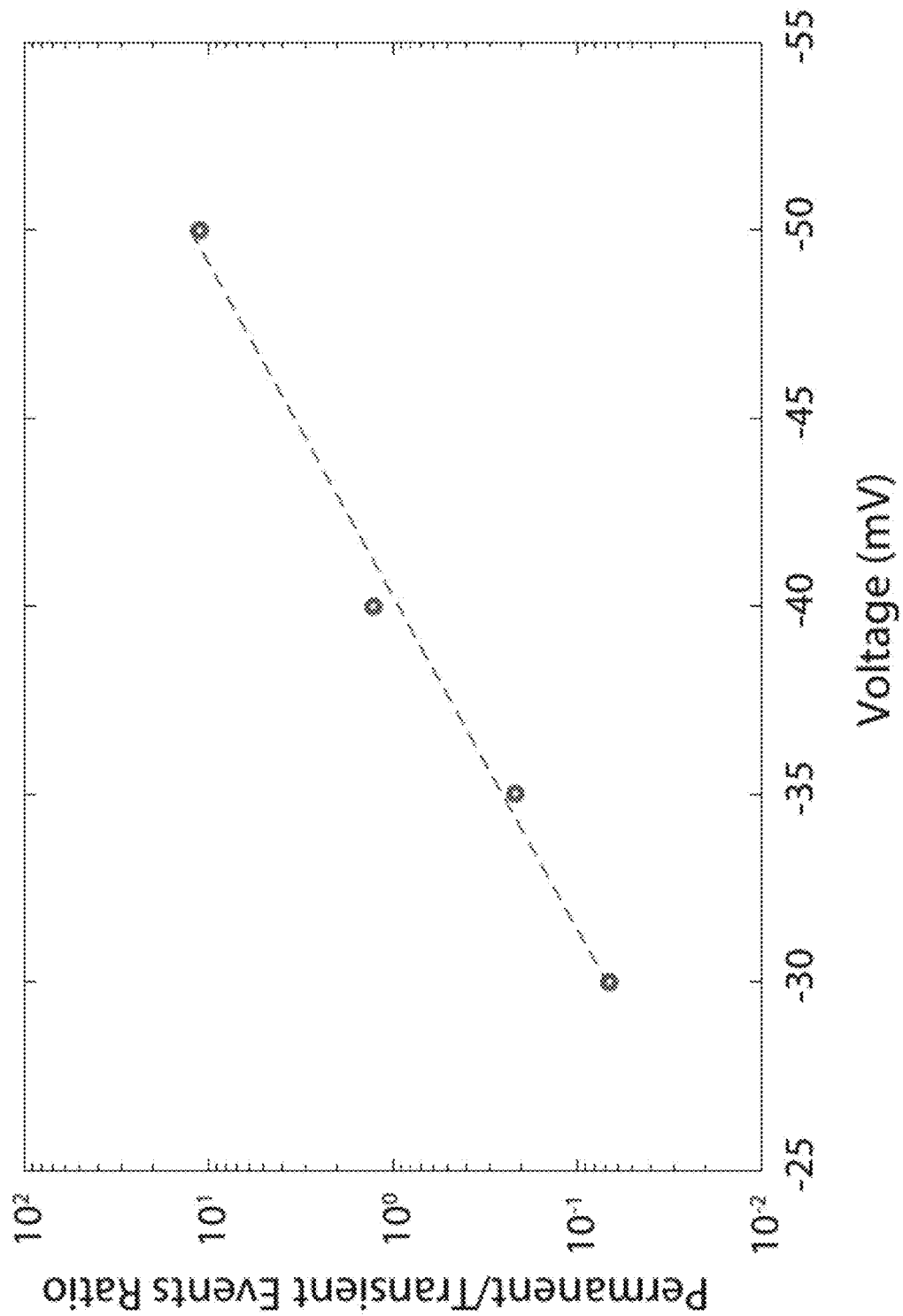
FIG. 12 shows an X-Y plot of a ratio of permanent events to transient events as a function of voltage.

For the 1.66 nS pore FIGS. 10A-10F show that the level populations in the PDL's are also strongly voltage-bias dependent. This effect is dramatically indicated by plotting the ratio of the number of Permanent events to the number of Transient events as a function of applied bias voltage. This is shown in FIG. 12. Increasing the bias voltage from 30 mV to 50 mV results in dramatic increase in this ratio. At high bias voltage, the energy landscape of the protein in the pore is clearly biased towards permanently capturing the Avidin to the deepest level in the pore from which escape eventually becomes impossible.

FIG. 12 demonstrates that the PDL method of analysis provided herein enables the revealing of details that are very specific to particular properties, such as orientation of the protein in the nanopore as well as target molecules shuttled to the nanopore by the protein. Together with the experimental methods provided herein, the analysis method thereby provides a powerful technique for achieving single-molecule characterization with the nanopore-based platform provided herein.

For the Avidin-biotin complex, the current blockage for the deeply trapped level is decreased by 4% relative to that for Avidin alone. This is shown in the plot in FIG. 13. Since the deep blockage level for Avidin is independent of voltage in the −30 mV to −35 mV range, the difference in deep blockage levels can be due to a slightly bigger size for the biotin-Avidin complex.

FIGS. 14A-14G show exemplary Gaussian fits to the PDL histogram plots, according to an embodiment of the present disclosure. The positions of discrete blockage levels can be obtained from fits to blockage spectra in a PDL plot. For the PDL plot for transient events at −35 mV (FIG. 10C above), the levels below the 80% permanent level (AC80) can be obtained by fitting a sum of four Gaussians to each spectrum for blockages below 65%. FIGS. 14A-14G show exemplary Gaussian fits to the PDL histogram plots of FIGS. 10A-10F.

To produce the efficient convergence of the fitting routine of FIGS. 14A-14G, the following procedure can be used: First the spectrum for $\tau_{trans}$=1000 ms is considered. One Gaussian can be fitted to the spectrum in a restricted blockage region around the dominant 57% peak, and then subtract the resulting Gaussian from the data. The result of this subtraction shows the 52% peak clearly. Another Gaussian can be fitted in a blockage region around that peak and again the resulting Gaussian can be subtracted. This reveals the 45% peak which is fitted with a Gaussian in a restricted blockage region. The resulting values for the position and width of the two Gaussians centered at 57% (AC57) and 45% (AC45) are then used as fixed values for fits with four Gaussians to all spectra over the whole blockage region below 65%. The result of the fits and the values of positions, widths, and amplitudes of each Gaussian component are shown in FIGS. 14A-14G.

The results of the fitting procedure for the position (Pos), width (Sigma), and amplitude (Amp) of each peak and for each spectrum are shown in Table 3, below.

TABLE 3

Amplitude, Position, and Widths for
Gaussian Distributions of PDL Plots

| | AC40 | | | AC45 | AC52 | | | AC57 |
|---|---|---|---|---|---|---|---|---|
| $\tau_{rans}$ | Amp | Pos | Sigma | Amp | Amp | Pos | Sigma | Amp |
| 1000 | 817 ± 434 | 0.4001 ± 0.012 | 0.0178 ± 0.012 | 1792 ± 411 | 3068 ± 351 | 0.5272 | 0.0371 | 20422 ± 373 |
| 500 | 847 ± 251 | 0.4024 ± 0.008 | 0.0194 ± 0.008 | 1531 ± 285 | 3818 ± 213 | 0.5272 | 0.0371 | 16914 ± 232 |
| 100 | 809 ± 78 | 0.4080 ± 0.004 | 0.0240 ± 0.004 | 808 ± 165 | 3561 ± 69 | 0.5272 | 0.0371 | 4506 ± 74 |
| 30 | 644 ± 28 | 0.4069 ± 0.002 | 0.0247 ± 0.001 | 537 ± 61 | 1793 ± 23 | 0.5181 | 0.0333 | 1069 ± 23 |
| 10 | 370 ± 12 | 0.4058 ± 0.001 | 0.0248 ± 0.001 | 228 ± 27 | 468 ± 10 | 0.5106 | 0.0321 | 185 ± 10 |
| 5 | 207 ± 9 | 0.4012 ± 0.001 | 0.0240 ± 0.001 | 136 ± 15 | 172 ± 8 | 0.5106 | 0.0321 | 44 ± 7 |
| 2 | 69 ± 3 | 0.3996 ± 0.001 | 0.0248 ± 0.001 | 33 ± 5 | 29 ± 2 | 0.5106 | 0.0321 | 3 ± 2 |

The entrance level can be first identified from a plurality of the individual permanent event's current signatures. Then in the PDL for permanent events, the presence of the entrance level is confirmed by the appearance of a peak at lower blockage level (i.e., 57% for Avidin) than the 80% permanent blockage level (also for Avidin). The presence of this lower peak in all spectra within a permanent-event PDL for Avidin, and the absence of the other peaks found in the transient-event PDL (the peaks at 40%, 45%, 52%) prompts the conclusion that a particular orientation of Avidin relative to the nanopore is required for permanent trapping. (The position of the peak positions are determined by fitting with sums of Gaussians to individual spectra within a PDL). These levels and conclusion are for Avidin in ClyA, which are just one example of using the PDL analysis and visualization of the dynamics and or interaction of proteins.

Examples

ClyA Monomer Expression and Purification

All reagents can be purchased from Fisher Scientific and/or Boston Bioproducts unless otherwise stated. Phenylmethane sulfonyl fluoride (PMSF) and magnesium chloride were purchased from Sigma. The gradient 4-15% gels were purchased from Bio-rad and the detergent n-Dodecyl-β-D-maltopyranoside (DDM) was purchased from EMD Millipore.

C-terminal His6 tagged ClyAwt protein was expressed in BL21 (DE3) cells. Specifically, pT7-ClyAwt-CHis6 plasmid was transformed in BL21 (DE3) chemically competent cells and grown on LB-Amp Agar plates. One colony was inoculated in starter LB media containing 100 µg/ml ampicillin antibiotic and grown at 37° C. with shaking at 200 rpm. The starter culture was used to inoculate 250 ml LB media containing 100 µg/ml ampicillin. The culture was grown at 37° C. until the OD600 was between 0.5 and 0.65. The culture was then cooled on ice and induced by adding IPTG to a final concentration of 0.5 mM and then incubated for 16 hrs at 15° C. with shaking. After 16 hrs, the culture was harvested at 3100×g and the pellet re-suspended in 15 ml of 50 mM Tris-HCl pH 8.0, 1 mM EDTA buffer and frozen in −20° C. until ready to use.

The frozen pellet was subsequently thawed at room temperature and a final concentration of 0.5 mM PMSF was added. The mixture was sonicated on ice to lyse the cells. MgCl2 was added to the lysate at a final concentration of 10 mM and the mixture was then centrifuged for 20 mins at 20,000×g. The supernatant was filtered through a 0.22 µm filter membrane and loaded onto a gravity NiNTA column equilibrated with buffer A (150 mM NaCl, 50 mM Tris-HCl pH 8). The column was then subsequently washed with buffer A to remove unbound proteins. Buffer A1 (150 mM NaCl, 50 mM Tris-HCl, 50 mM imidazole) was used to wash the weakly bound proteins and then the ClyA protein was eluted and collected in buffer A2 (150 mM NaCl, 50 mM Tris-HCl, 150 mM imidazole).

The eluted ClyA proteins were dialyzed using a 6-8 kDa cutoff membrane with constant stirring at 4° C. for two cycles in dialysis buffer (150 mM NaCl, 50 mM Tris-HCl, 5 mM EDTA). The proteins were then concentrated using a 10 kDa cutoff centricon to −3 ml and loaded onto a gel filtration column equilibrated in 150 mM NaCl, 20 mM sodium phosphate pH 7.0 buffer to remove aggregated proteins. The ClyA monomer was collected and kept at 4° C. for 2 weeks or in −80° C. for long-term storage.

Preparation and Purification of ClyA Oligomers (Nanopores)

Purified ClyA monomers were next suspended at 0.6 mg/mL in a buffered solution containing 50 mM NaCl, 10 mM sodium phosphate pH 7.4 (with a buffer exchange column). Oligomeric ClyA was formed from monomers by the addition of n-Dodecyl beta-D-maltoside (DDM, Calbiochem/EMD Millipore; 10% w/v in water) to a final concentration of 1% and incubated 20 min at room temperature.

ClyA nanopore purification was carried out by blue native gel electrophoresis using a 4-16% polyacrylamide gradient gel (NativePAGE, Invitrogen/Novex Life Technologies). Typically, 10 ug of ClyA oligomers were combined with electrophoresis loading buffer and applied to a 1.0 mm×5.0 mm sample well of the gel. Major bands of oligomeric ClyA were excised from the gel following electrophoresis, and nanopores were recovered from the gel slices by diffusion into an elution buffer containing 150 mM NaCl, 0.2% DDM, 50 mM Tris-Cl pH 8.0.

Avidin Preparation

Lyophilized purified Avidin from hen egg white (Pierce/Thermo Scientific Product #21121) was weighed and dissolved in deionized water to 2 mg/mL concentration. For subsequent storage at 4 C, an equal volume of 2× Phosphate Buffered Saline with 20% glycerol was added to the suspension to bring the Avidin stock solution concentration to a nominal 1 mg/mL. Prior to use in ClyA nanopore experiments, an aliquot of the Avidin stock solution was applied to a Bio-Spin 30 spin column (Bio-Rad Laboratories) equilibrated with 150 mM NaCl, 15 mM Tris-Cl pH 7.5 for buffer exchange.

Preparation of d-Biotin

An approximately 1 mM biotin solution was prepared by dissolving 0.2 mg d-Biotin (Sigma-Aldrich/Millipore Sigma) per mL of 20 mM KCl, 50 mM Tris-Cl pH 7.5.

The nanopore-matched protein shuttle described above is not limited to the Avidin-ClyA protein-nanopore example. The study of protein and target molecule structure, dynamics, and enzymatic activity more generally is enabled herein by a nanopore that has an inner lumen diameter that is substantially the same or less than the diameter of a protein, for some protein configuration and for at least one site along the nanopore length. Permanent capture of the protein in the nanopore is enabled herein and can be exploited for study of the protein and target molecules provided in the molecular shuttle. In a corresponding methodology, a protein shuttle and a target molecule are captured at or at least partially in a nanopore, studied, and then ejected from the nanopore. The low current noise observed for deeply-trapped Avidin and an Avidin-biotin complex indicates that this system provides a quiet background for studying electrical signals that are induced by the target molecule and/or substrates interacting with the target molecule and/or products produced by such interaction. An Avidin-biotin complex employed in a molecular shuttle thereby enables control of target molecule study at a level heretofore unachievable.

While various examples of the present invention have been described above, it should be understood that they have been presented by way of example only, and not limitation. Numerous changes to the disclosed examples can be made in accordance with the disclosure herein without departing from the spirit or scope of the invention. Thus, the breadth and scope of the present invention should not be limited by any of the above described examples. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular examples only and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method for characterizing shuttle capture in a nanopore sensor, comprising:
   collecting a plurality of time-dependent current blockage signatures for a selected bias voltage;
   calculating, based on the plurality of time-dependent current blockage signatures, a duration of a shuttle capture event and an average blockage percentage for the shuttle capture event;
   determining a blockage level based on a distribution characteristic of the plurality of time-dependent current blockage signatures.

2. The method of claim 1, wherein the determining further comprises whether the duration of the shuttle capture event falls in a range between a pre-defined minimum duration and a pre-defined maximum duration.

3. The method of claim 1, wherein the determining further comprises identifying a particular blockage event as permanent if the duration of the particular blockage event is larger than a threshold time.

4. The method of claim 3, wherein the threshold time is any period of time larger than 500 milliseconds.

5. The method of claim 2, wherein the pre-defined minimum duration is 0 milliseconds and the pre-defined maximum duration is 2 milliseconds.

6. The method of claim 5, wherein the plurality of time-dependent current blockage signatures provides a blockage peak at 40% current blockage.

7. The method of claim 2, wherein the pre-defined minimum duration is 0 milliseconds and the pre-defined maximum duration is 5 milliseconds.

8. The method of claim 7, wherein the plurality of time-dependent current blockage signatures provides blockage peaks at 45% and 52% current blockage.

9. The method of claim 2, wherein the pre-defined minimum duration is 0 milliseconds and the pre-defined maximum duration is 10 milliseconds.

10. The method of claim 9, wherein the plurality of time-dependent current blockage signatures provides blockage peaks at 40%, 45%, and 52% current blockage.

11. The method of claim 2, wherein the pre-defined minimum duration is 0 milliseconds and the pre-defined maximum duration is 30 milliseconds.

12. The method of claim 11, wherein the plurality of time-dependent current blockage signatures provides a blockage peak at 57% current blockage.

13. The method of claim 2, wherein the pre-defined minimum duration is 0 milliseconds and the pre-defined maximum duration is 100 milliseconds.

14. The method of claim 13, wherein the plurality of time-dependent current blockage signatures provides blockage peaks at 40%, 45%, 52%, and 57% current blockage.

15. The method of claim 2, wherein the pre-defined minimum duration is 0 milliseconds and the pre-defined maximum duration is 500 milliseconds.

16. The method of claim 15, wherein the plurality of time-dependent current blockage signatures provides blockage peaks at 40%, 45%, 52%, and 57% current blockage.

17. The method of claim 2, wherein the pre-defined minimum duration is 0 milliseconds and the pre-defined maximum duration is 1000 milliseconds.

18. The method of claim 17, wherein the plurality of time-dependent current blockage signatures provides a blockage peak at 80% current blockage.

19. The method of claim 2, further comprising identifying an expected protein molecule orientation based on at least one of a comparison of protein dynamics landscapes (PDLs)

for transient and permanent events and a presence or absence of blockage peaks for individual spectra with the PDLs for transient and permanent events, wherein each PDL comprises a collection of blockage spectra, wherein each of the collection of blockage spectra comprises a histogram of blockage values for events of a selected maximum duration.

* * * * *